(12) United States Patent
Mjalli et al.

(10) Patent No.: US 7,329,684 B2
(45) Date of Patent: *Feb. 12, 2008

(54) BENZIMIDAZOLE DERIVATIVES AS THERAPEUTIC AGENTS

(75) Inventors: Adnan M. M. Mjalli, Jamestown, NC (US); Ramesh Gopalaswamy, Jamestown, NC (US)

(73) Assignee: TransTech Pharma, Inc., High Point, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/225,277

(22) Filed: Sep. 13, 2005

(65) Prior Publication Data

US 2006/0025464 A1    Feb. 2, 2006

Related U.S. Application Data

(63) Continuation of application No. 10/091,609, filed on Mar. 5, 2002, now Pat. No. 7,087,632.

(60) Provisional application No. 60/273,377, filed on Mar. 5, 2001.

(51) Int. Cl.
A61K 31/4184 (2006.01)
C07D 235/14 (2006.01)

(52) U.S. Cl. .................................. 514/394; 548/309.7

(58) Field of Classification Search ............. 548/309.7; 514/394

See application file for complete search history.

(56) References Cited

U.S. PATENT DOCUMENTS

| | | | |
|---|---|---|---|
| 3,255,202 A | 6/1966 | Johnson et al. | |
| 3,951,968 A | 4/1976 | Fauran et al. | |
| 4,166,452 A | 9/1979 | Generales, Jr. | |
| 4,265,874 A | 5/1981 | Bonsen et al. | |
| 4,356,108 A | 10/1982 | Schwab et al. | |
| 4,873,313 A | 10/1989 | Crawford et al. | |
| 5,202,424 A | 4/1993 | Vlassara et al. | |
| 5,585,344 A | 12/1996 | Vlassara et al. | |
| 5,688,653 A | 11/1997 | Ulrich et al. | |
| 5,703,092 A | 12/1997 | Xue et al. | |
| 5,864,018 A | 1/1999 | Morser et al. | |
| 5,922,770 A | 7/1999 | Peschke et al. | |
| 5,939,526 A | 8/1999 | Gaugler et al. | |
| 6,100,098 A | 8/2000 | Newkirk | |
| 6,316,474 B1 | 11/2001 | McCauley et al. | |
| 7,087,632 B2 * | 8/2006 | Mjalli et al. ................. | 514/394 |

FOREIGN PATENT DOCUMENTS

| | | |
|---|---|---|
| FR | 1 476 560 | 4/1967 |
| FR | 2 160 719 | 7/1973 |
| GB | 2 005 674 | 4/1979 |
| WO | WO95/09838 | 4/1995 |
| WO | WO95/35279 | 12/1995 |
| WO | WO96/32385 | 10/1996 |
| WO | WO97/22618 | 6/1997 |
| WO | WO97/26913 | 7/1997 |
| WO | WO97/39121 | 10/1997 |
| WO | WO97/39125 | 10/1997 |
| WO | WO98/22138 | 5/1998 |
| WO | WO98/27108 | 6/1998 |
| WO | WO98/33492 | 8/1998 |
| WO | WO99/07402 | 2/1999 |
| WO | WO99/18987 | 4/1999 |
| WO | WO99/25690 | 5/1999 |
| WO | WO99/50230 | 10/1999 |
| WO | WO99/54485 | 10/1999 |
| WO | WO 00/20458 | 4/2000 |
| WO | WO 00/20621 | 4/2000 |
| WO | WO 01/12598 | 2/2001 |

OTHER PUBLICATIONS

Albercio, F. & Carpino, L.A., "Coupling Reagents and Activation" *Methods in Enzymology* 289:104-126, Academic Press, San Diego (1997).

Barton, J.W., "In Protection of N-H bonds and $NR_3$" *Protective Groups in Organic Chemistry*, J.F.W. McOmie, ED., Plenum Press, New York, NY (1973).

Berge, S.M., et al., "Pharmaceutical Salts" *Journal of Pharmaceutical Sciences* 66:1-19 (1977).

Chitaley, K., et al., "Antagonism of Rho-Kinase Stimulates Rate Penile Erection via a Nitric Oxide-Independent Pathway" *Nature Medicine* 7:119-122 (2002).

Degenhardt, T.P., et al., "Chemical Modification of Proteins by Methylglyoxal" *Cell Mol. Biol.*, 44:1139-1145 (1998).

Dyer, D.G., et al., "Accumulation of Maillard Reaction Products in Skin Collagen in Diabetes and Aging" *J. Clin. Invest.*, 91:2463-2469 (1993).

Dyer, D.G., et al., "Formation of Pentosidine during Nonenzymatic Browning of Proteins by Glucose" *J. Biol. Chem.*, 266:11654-11660 (1991).

(Continued)

*Primary Examiner*—Laura L. Stockton
(74) *Attorney, Agent, or Firm*—Samuel B. Rollins

(57) ABSTRACT

This invention provides certain compounds, methods of their preparation, pharmaceutical compositions comprising the compounds, and their use in treating human or animal disorders. The compounds of the invention are useful as modulators of the interaction between the receptor for advanced glycated end products (RAGE) and its ligands, such as advanced glycated end products (AGEs), S100/calgranulin/EN-RAGE, β-amyloid and amphoterin, and for the management, treatment, control, or as an adjunct treatment for diseases in humans caused by RAGE. Such diseases or disease states include acute and chronic inflammation, the development of diabetic late complications such as increased vascular permeability, nephropathy, atherosclerosis, and retinopathy, the development of Alzheimer's disease, erectile dysfunction, and tumor invasion and metastasis.

23 Claims, No Drawings

OTHER PUBLICATIONS

Greene, T.W., "Protection for the Amino Group" *Protective Groups in Organic Synthesis*, John Wiley and Sons, New York, NY, Chapter 7 (1981).

Hammes, H.P., et al., "Diabetic Retinopathy Risk Correlates with Intracellular Concentrations of the Glycoxidation Product $N^C$-(Carboxymethyl) Lysine Independently of Glycohaemoglobin Concentrations" Diabetologia, 42:603-607 (1999).

Hoffman, M.A., et al., "RAGE Mediates a Novel Proinflammatory Axis: A Central Cell Surface Receptor for S100/Calgranulin Polypeptides" *Cell*, 97:889-901(1999).

Hori, O., et al., "The Receptor for Advanced Glycation End Products (RAGE) is a Cellular Binding site for Amphoterin" *J. Biol. Chem.*, 270:25752-761 (1995).

Huttunen, H.J., et al., "Receptor for Advanced Glycation End Products (RAGE)-Mediated Neurite Outgrowth and Activation of NF-Kappa B Require the Cytoplasmic Domain of the Receptor But Different Downstream Signaling Pathways" *J. Biol. Chem.* 274(28):19919-24 (1999).

Kumar, S.R., et al., "RAGE at the Blood-Brain Barrier Mediates Neurovascular' Dysfunction Caused by Amyloid$\beta_{1-40}$ Peptide" *Neurosci. Program*, 141-#255.19 (2000).

Leder, A. et al., "v-HA-*ras* Transgene Abrogates the Initiation Step in Mouse Skin Tumorigenesis: Effects of Phorbol Esters and Retinoic Acid" *Proc. Natl. Acad. Sci., USA*, 87:9178-9182 (1990).

Li, J. et al., "Sp1-Binding elements in the Promoter of RAG Are Essential for Amphoterin-Mediated Gene Expression in Cultured Neuroblastoma Cells." *J. Biol. Chem.*, 273:30870-30878 (1998).

Li, J. et al., "Characterization and Functional Analysis of the Promoter of RAGE, the Receptor for Advanced Glycation End Products," *J. Biol. Chem.*, 272:16498-16506 (1997).

Lugering, N. et al., "The Myeloic Related Protein MRP8/14 (27E10 Antigen)- Usefulness as a Potential Marker for Disease Activity in Ulcerative Colitis and Putative Biological Function" Eur. J. Clin. Invest., 25:659-664 (1995).

Miyata, T. et al., "$\beta$2-Microglobulin Modified with Advanced Glycation End Products Is a Major Component of Hemodialysis-Associated Amyloidosis" *J. Clin. Invest.*, 92:1243-1252 (1993).

Miyata, T. et al., "The Receptor for Advanced Glycation End Products (RAGE) is a Central Mediator of the Interaction of AGE-$\beta_2$Microglobulin with Human Mononuclear Phagocytes Via an Oxidant-Sensitive Pathway" *J. Clin. Invest*, 98:1088-1094 (1996).

Neeper, M., et al., "Cloning and Expression of a Cell Surface Receptor for Advanced Glycosylation End Products of Proteins" *J. Biol. Chem.*, 267:14998-15004 (1992).

Parkkinen, J. et al., "Amphoterin, the 30-kDa Protein in a Family of HMG1-Type Polypeptides" *J. Biol Chem.*, 268:19726-19738 (1993).

Rammes, A. et al., Myeloid-Related Protein (MRP) 8 and MRP 14, Calcium-Binding Proteins of the S100 Family, Are Secreted by Activated Monocytes via a Novel, Tubulin-Dependent Pathway *J. Biol. Chem.*, 272:9496-9502 (1997).

Rauvala, H. et al., "Isolation and Some Characteristics of an Adhesive Factor of Brain That Enhances Neurite Outgrowth in Central Neurons" *J. Biol. Chem.*, 262:16625-16635 (1987).

Reddy, S. et al., "$N^C$-(Carboxymethyl) Lysine Is a Dominant Advanced Glycation End Product (AGE) Antigen in Tissue Proteins" *Biochem.*, 34:10872-10878 (1995).

Schafer, B.W., et al., "The S100 Family of EF-Hand Calcium-Binding Proteins: Functions and Pathology" *TIBS*, 21:134-140 (1996).

Schleicher, E.D., et al., "Increased Accumulation of the Glycoxidation Product $N^C$-(Carboxymethyl) Lysine in Human Tissues in Diabetes and Aging" *J. Clin. Invest.*, 99(3):457-468 (1997).

Schmidt, A.M. et al., "The Dark Side of Glucose" *Nature Med.*, 1:1002-1004 (1995).

Schmidt, A.M., et al, "The V-Domain of Receptor for Advanced Glycation Endproducts (RAGE) Mediates Binding of AGEs: A Novel Target for Therapy of Diabetic Complications:" *Supplement to Circulation* vol. 96, #194 (1997).

Taguchi, A. et al., "Blockade of RAGE-Amphoterin Signalling Suppresses Tumour Growth and Metastases" *Nature*, 405:354-360 (2000).

Tanaka, N., et al., "The Receptor for Advanced Glycation End Products is Induced by the Glycation Products Themselves and Tumor Necrosis Factor-$\alpha$ through Nuclear Factor-$_k$ B, and by 17$\beta$-Estradoil through Sp-1 in Human Vascular Endothelial Cells" J. Biol. Chem.., 275:25781-25790 (2000).

Teillet et al., "Food Restriction Prevents Advanced Glycation End Product Accumulation and Retards Kidney Aging in Lean Rats" J. Am. Soc. Nephrl., 11:1488-1497 (2000).

Vlassara H., "Advanced Glycatin End-Products and Atherosclerosis" the Finnish Medical Society Duodecim, Ann. Med., 28:419-426 (1996).

Wautier et al., "Receptor-Mediateed $Endothelial Cell Dysfunction in diabetic Vasculopathy: Soluble Receptor for Advanced Glycation End Products Blocks Hyperpermeability in Diabetic Rats" J. Clin. Invest., 97: 238-243 (1996).

Yan, S.-D., et al., "RAGE and Amyloid-$\beta$ Peptide Neurotoxicity in alzheimer's Disease" Nature 382;685-691 (1996).

Yan, S.-D., et al., "An Intracellular Protein that Binds Amyloid-$\beta$ Peptide and Mediated Neurotoxicity in Alzheimer's Disease" Nature, 389:689-695 (1997).

Yan, S.-D. et al., "Amyloid-$\beta$ Peptide-Receptor for Advanced Glycation Endproduct Interaction Elicits Neuronal Expression of Macrophage-Colony Stimulating Factor: A Proinflammatory Pathway in Alzheimer Disease" Proc. Natl. Acad. Sci., USA 94:5296-5301 (1997).

Yan, S.-D et al., "Receptor-Dependent Cell Stress and Amyloid Accumulation inSystemic Amyloidosis" Nat. Med. 6:643-651 (2000).

Zimmer et al., "The S100 Protein Family: History, Function, and Expression" Brain Res. Bull, 37:417-429 (1995).

International Search Report for PCT/US01/17251 dated Aug. 14, 2001.

Golub et al., Science, vol. 286, pp. 531-537, Oct. 15, 1997.

PCT Notification of Transmittal of the International Search Report corresponding to PCT application from PCT/US02/06706, Jun. 26, 2002.

CA Registry No. 366489-63-6, Nov. 2, 2001.
CA Registry No. 366489-61-4, Nov. 2, 2001.
CA Registry No. 366489-58-9, Nov. 2, 2001.
CA Registry No. 366489-56-7, Nov. 2, 2001.
CA Registry No. 366489-47-6, Nov. 2, 2001.
CA Registry No. 366489-45-4, Nov. 2, 2001.
CA Registry No. 366489-42-1, Nov. 2, 2001.
CA Registry No. 366489-40-9, Nov. 2, 2001.
CA Registry No. 338410-76-7, May 25, 2001.
CA Registry No. 338410-71-2, May 25, 2001.
CA Registry No. 338410-59-6, May 25, 2001.
CA Registry No. 338410-56-3, May 25, 2001.
CA Registry No. 338410-55-2, May 25, 2001.
CA Registry No. 338410-51-8, May 25, 2001.
CA Registry No. 138369-72-9, Jan. 18, 1992.
CA Registry No. 138369-70-7, Jan. 18, 1992.
Mengelberg, CA 53: 15063h, 1959.
Salgonkar et al., Indian Drugs, 37(11), pp. 547-550 (2000).
Balboni et al., CA 134:66089, (2000).
Yalabe et al., CA 129:95714, (1998).
Hoom et al., CA 127:336383, (1997).
Casella et al., CA 122:95181, (1995).
Varney et al., Journal of Medicinal Chemistry 37(15), pp. 2274-2284 (1994).
Nawwar et al., CA 119:250418, (1993).
Crane et al., CA 116:50261, (1992).
Cuadro et al., CA 109;128908, (1988).
Kamdar et al., CA 109: 128903, (1998).
Aminabhavi et al., VA 107:23874, (1987).
Nandi et al., CA 106:138323 (1987).
Ohlani et al., CA 87:178868, (1977).
Maekawa et al., CA 85:154963, (1976).
Tiwari et al., CA 85:46510, (1976).
Maekawa et al., CA 85:21787, (1976).

Schubert et al., CA 81:120538, (1974).
Guaitieri et al., Journal of Medicinal Chemistry, 15(4) pp. 420-422, (1972).
Schubert et al., CA 74:1119761, (1971).

Kanadea et al., CA 72:55332, (1970).
Aryuzina et al., CA 66: 94952, (1967).

* cited by examiner

BENZIMIDAZOLE DERIVATIVES AS THERAPEUTIC AGENTS

STATEMENT OF RELATED APPLICATION

This application is a continuation application of application Ser. No. 10/091,609, filed Mar. 5, 2002 now U.S. Pat. No. 7,087,632, which claims the benefit of priority of U.S. Provisional Application: Ser. No. 60/273,377, filed Mar. 5, 2001, the entirety of which are herein incorporated by reference.

FIELD OF THE INVENTION

This invention relates to compounds which are modulators of the receptor for advanced glycated end products (RAGE) and interaction with its ligands such as advanced glycated end products (AGEs), S100/calgranulin/EN-RAGE, β-amyloid and amphoterin, for the management, treatment, control, or as an adjunct treatment of diseases caused by RAGE.

BACKGROUND OF THE INVENTION

Incubation of proteins or lipids with aldose sugars results in nonenzymatic glycation and oxidation of amino groups on proteins to form Amadori adducts. Over time, the adducts undergo additional rearrangements, dehydrations, and cross-linking with other proteins to form complexes known as Advanced Glycosylation End Products (AGEs). Factors which promote formation of AGEs included delayed protein turnover (e.g. as in amyloidoses), accumulation of macromolecules having high lysine content, and high blood glucose levels (e.g. as in diabetes) (Hori et al., *J. Biol. Chem.* 270: 25752-761, (1995)). AGEs have implicated in a variety of disorders including complications associated with diabetes and normal aging.

AGEs display specific and saturable binding to cell surface receptors on endothelial cells of the microvasculature, monocytes and macrophages, smooth muscle cells, mesengial cells, and neurons. The Receptor for Advanced Glycated Endproducts (RAGE) is a member of the immunoglobulin super family of cell surface molecules. The extracellular (N-terminal) domain of RAGE includes three immunoglobulin-type regions, one V (variable) type domain followed by two C-type (constant) domains (Neeper et al., *J. Biol. Chem.* 267:14998-15004 (1992). A single transmembrane spanning domain and a short, highly charged cytosolic tail follow the extracellular domain. The N-terminal, extracellular domain can be isolated by proteolysis of RAGE to generate soluble RAGE (sRAGE) comprised of the V and C domains.

RAGE is expressed in most tissues, and in particular, is found in cortical neurons during embryogenesis (Hori et al., *J. Biol. Chem.* 270:25752-761 (1995)). Increased levels of RAGE are also found in aging tissues (Schleicher et al., *J. Clin. Invest.* 99 (3): 457-468 (1997)), and the diabetic retina, vasculature and kidney (Schmidt et al., *Nature Med.* 1:1002-1004 (1995)). Activation of RAGE in different tissues and organs leads to a number of pathophysiological consequences. RAGE has been implicated in a variety of conditions including: acute and chronic inflammation (Hofmann et al., *Cell* 97:889-901 (1999)), the development of diabetic late complications such as increased vascular permeability (Wautier et al., *J. Clin. Invest.* 97:238-243 (1995)), nephropathy (Teillet et al., *J. Am. Soc. Nephrol.* 11:1488-1497 (2000)), atherosclerosis (Vlassara et. al., *The Finnish Medical Society DUODECIM, Ann. Med.* 28:419-426 (1996)), and retinopathy (Hammes et al., *Diabetologia* 42:603-607 (1999)). RAGE has also been implicated in Alzheimer's disease (Yan et al., *Nature* 382: 685-691, (1996)), erectile dysfunction, and in tumor invasion and metastasis (Taguchi et al., *Nature* 405: 354-357, (2000)).

In addition to AGEs, other compounds can bind to, and modulate RAGE. In normal development, RAGE interacts with amphoterin, a polypeptide which mediates neurite outgrowth in cultured embryonic neurons (Hori et al., 1995). RAGE has also been shown to interact with EN-RAGE, a protein having substantial similarity to calgranulin (Hofmann et al., *Cell* 97:889-901 (1999)). RAGE has also been shown to interact with β-amyloid (Yan et al., *Nature* 389: 589-595, (1997); Yan et al., *Nature* 382:685-691 (1996); Yan et al., *Proc. Natl. Acad. Sci.*, 94:5296-5301 (1997)).

Binding of ligands such as AGEs, S100/calgranulin/EN-RAGE, β-amyloid, CML ($N^\epsilon$-Carboxymethyl lysine), and amphoterin to RAGE has been shown to modify expression of a variety of genes. For example, in many cell types interaction between RAGE and its ligands generates oxidative stress, which thereby results in activation of the free radical sensitive transcription factor NF-κB, and the activation of NF-κB regulated genes, such as the cytokines IL-1β, TNF-α, and the like. In addition, several other regulatory pathways, such as those involving p21ras, MAP kinases, ERK1 and ERK2, have been shown to be activated by binding of AGEs and other ligands to RAGE. In fact, transcription of RAGE itself is regulated at least in part by NF-κB. Thus, an ascending, and often detrimental, spiral is fueled by a positive feedback loop initiated by ligand binding. Antagonizing binding of physiological ligands to RAGE, therefore, is our target for down-regulation of the pathophysiological changes brought about by excessive concentrations of AGEs and other ligands for RAGE.

Thus, there is a need for the development of compounds that antagonize binding of physiological ligands to the RAGE receptor.

SUMMARY OF THE INVENTION

This invention provides certain substituted benzimidazole compounds. Embodiments of the present invention provides compound of Formula (I) as depicted below; methods of their preparation; pharmaceutical compositions comprising the compounds; and methods for their use in treating human or animal disorders. Compounds of the invention are useful as modulators of the interaction of the receptor for advanced glycated end products (RAGE) with its ligands such as advanced glycated end products (AGEs), S100/calgranulin/EN-RAGE, β-amyloid and amphoterin. The compounds are useful in a variety of applications including for the management, treatment, control, and/or as an adjunct of diseases in humans caused by RAGE. Such diseases or disease states include acute and chronic inflammation, the development of diabetic late complications such as increased vascular permeability, nephropathy, atherosclerosis, and retinopathy, the development of Alzheimer's disease, erectile dysfunction, and tumor invasion and metastasis.

DETAILED DESCRIPTION OF THE INVENTION

In a first aspect, the present invention provides certain substituted benzimidazole compounds. Such compounds are useful in the modulation, preferably in the inhibition, of the interaction of RAGE with its physiological ligands, as will be discussed in more detail below.

In a second aspect, the present invention provides compounds of Formula (I):

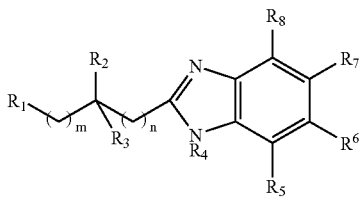

wherein
m is an integer of from 0 to 3;
n is an integer of from 0 to 3;
$R_1$ comprises aryl;
$R_2$ comprises
  a) a group of the formula —$N(R_9R_{10})$, —$NHC(O)R_9$, or —$NHC(O)OR_9$;
  b) a group of the formula —$OR_9$;
  c) a group of the formula —$SR_9$, —$SOR_9$, —$SO_2R_9$, —$SO_2NHR_9$, or —$SO_2N(R_9R_{10})$;
     wherein $R_9$ and $R_{10}$ independently comprise
     1) —H;
     2) -Aryl;
     3) a group comprising
        a) —$C_{1-6}$ alkyl;
        b) —$C_{1-6}$ alkylaryl;

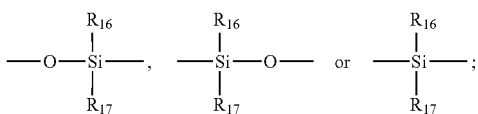

e) -aryl;
  f) —$C_{1-6}$ alkyl; or
  g) —$C_{1-6}$ alkylaryl;
$R_3$ and $R_4$ independently comprise
  a) H;
  b) -aryl;
  c) —$C_{1-6}$ alkyl;
  d) —$C_{1-6}$ alkylaryl; or
  e) —$C_{1-6}$ alkoxyaryl;
$R_5$, $R_6$, $R_7$, and $R_8$ independently comprise
  a) —H;
  b) —$C_{1-6}$ alkyl;
  c) -aryl;
  d) —$C_{1-6}$ alkylaryl;
  e) —$C(O)$—O—$C_{1-6}$ alkyl;
  f) —$C(O)$—O—$C_{1-6}$ alkylaryl;
  g) —$C(O)$—NH—$C_{1-6}$ alkyl;
  h) —$C(O)$—NH—$C_{1-6}$ alkylaryl;
  i) —$SO_2$—$C_{1-6}$ alkyl;
  j) —$SO_2$—$C_{1-6}$ alkylaryl;
  k) —$SO_2$-aryl;
  l) —$SO_2$—NH—$C_{1-6}$ alkyl;
  m) —$SO_2$—NH—$C_{1-6}$ alkylaryl;
  n) —$C(O)$—$C_{1-6}$ alkyl;
  o) —$C(O)$—$C_{1-6}$ alkylaryl;
  p) —Y—$C_{1-6}$ alkyl;
  q) —Y-aryl;
  r) —Y—$C_{1-6}$ alkylaryl;
  s) —Y—$C_{1-6}$ alkylene-$NR_{13}R_{14}$; or
  t) —Y—$C_{1-6}$ alkylene-W—$R_{15}$;
     wherein Y and W independently comprise —$CH_2$—, —O—, —N(H)—, —S—, $SO_2$—, —$CON(H)$—, —$NHC(O)$—, —$NHCON(H)$—, —$NHSO_2$—, —$SO_2N(H)$—, —$C(O)$—O—, —$NHSO_2NH$—, —O—CO—, $$-O-\underset{\underset{R_{17}}{|}}{\overset{\overset{R_{16}}{|}}{Si}}-,\ -\underset{\underset{R_{17}}{|}}{\overset{\overset{R_{16}}{|}}{Si}}-O-\ \text{or}\ -\underset{\underset{R_{17}}{|}}{\overset{\overset{R_{16}}{|}}{Si}}-;$$

$R_{16}$ and $R_{17}$ independently comprise aryl, $C_1$-$C_6$ alkyl, $C_1$-$C_6$ alkylaryl, $C_1$-$C_6$ alkoxy, or $C_1$-$C_6$ alkoxyaryl;
$R_{15}$ independently comprise aryl, $C_1$-$C_6$ alkyl, or $C_1$-$C_6$ alkylaryl; or
u) halogen, hydroxyl, cyano, carbamoyl, or carboxyl;
$R_{11}$, $R_{12}$, $R_{13}$, and $R_{14}$ independently comprise hydrogen, aryl, $C_1$-$C_6$ alkyl, $C_1$-$C_6$ alkylaryl, $C_1$-$C_6$ alkoxy, or $C_1$-$C_6$ alkoxyaryl;
$R_{13}$ and $R_{14}$ may be taken together to form a ring having the formula —$(CH_2)_o$—X—$(CH_2)_p$— bonded to the nitrogen atom to which $R_{13}$ and $R_{14}$ are attached, and/or $R_{11}$ and $R_{12}$ may, independently, be taken together to form a ring having the formula —$(CH_2)_o$—X—$(CH_2)_p$— bonded to the atoms to which $R_{11}$ and $R_{12}$ are connected, wherein o and p are, independently, 1, 2, 3, or 4; X comprises a direct bond, —$CH_2$—, —O—, —S—, —$S(O_2)$—, —$C(O)$—, —$CON(H)$—, —$NHC(O)$—, —$NHCON(H)$—, —$NHSO_2$—, —$SO_2N(H)$—, —$C(O)$—O— O—$C(O)$—, —$NHSO_2NH$—,

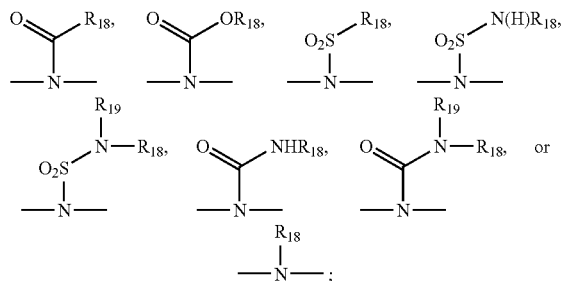

wherein the aryl and/or alkyl group(s) in $R_1$, $R_2$, $R_3$, $R_5$, $R_6$, $R_7$, $R_8$, $R_9$, $R_{10}$, $R_{11}$, $R_{12}$, $R_{13}$, $R_{14}$ $R_{15}$, $R_{16}$, $R_{17}$, $R_{18}$, and $R_{19}$ may be optionally substituted 1-4 times with a substituent group, wherein said substituent group(s) or the term substituted refers to groups comprising:
  a) —H;
  b) —Z—$C_{1-6}$ alkyl;
     —Z-aryl;
     —Z—$C_{1-6}$ alkylaryl;
     —Z—$C_{1-6}$-alkyl-$NR_{20}R_{21}$;
     —Z—$C_{1-6}$-alkyl-W—$R_{22}$;
     wherein Z and W independently comprise —$CH_2$—, —O—, —N(H), —S—, $SO_2$—, —$CON(H)$—, —$NHC(O)$—, —$NHCON(H)$—, —$NHSO_2$—, —$SO_2N(H)$—, —$C(O)$—O—, —$NHSO_2NH$—, —O—CO—, wherein;

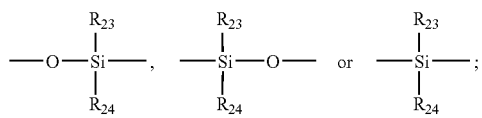

$R_{20}$ and $R_{21}$ independently comprise hydrogen, aryl, $C_1$-$C_6$ alkyl, $C_1$-$C_6$ alkylaryl, $C_1$-$C_6$ alkoxy, or $C_1$-$C_6$ alkoxyaryl;

$R_{22}$, $R_{23}$, and $R_{24}$ independently comprise aryl, $C_1$-$C_6$ alkyl, $C_1$-$C_6$ alkylaryl, $C_1$-$C_6$ alkoxy, or $C_1$-$C_6$ alkoxyaryl; or c) halogen, hydroxyl, cyano, carbamoyl, or carboxyl; and $R_{20}$ and $R_{21}$ may be taken together to form a ring having the formula —$(CH_2)_q$—X—$(CH_2)_r$— bonded to the nitrogen atom to which $R_{20}$ and $R_2$ are attached wherein q and r are, independently, 1, 2, 3, or 4; X comprises a direct bond, —$CH_2$—, —O—, —S—, —$S(O_2)$—, —C(O)—, —CON(H)—, —NHC(O)—, —NHCON(H)—, —$NHSO_2$—, —$SO_2N(H)$—, —C(O)—O—, —O—C(O)—, —$NHSO_2NH$—,

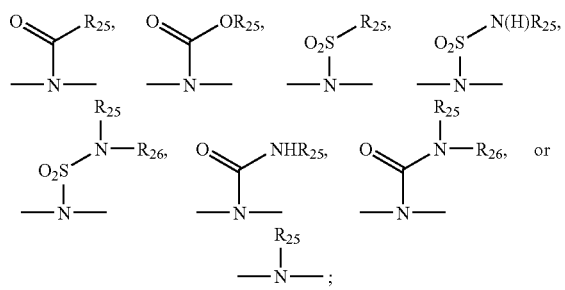

$R_{25}$, $R_{26}$, and $R_{27}$ independently comprise hydrogen, aryl, $C_1$-$C_6$ alkyl, or $C_1$-$C_6$ alkylaryl; or a pharmaceutically acceptable salt, solvate or prodrug thereof.

In a preferred embodiment the present invention comprises compounds wherein m is an integer of from 0 to 3; n is 0; $R_3$ is hydrogen, as represented by the formula (II)

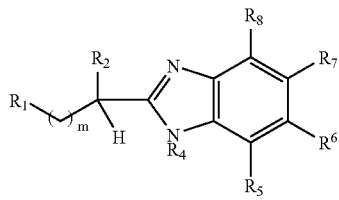

(II)

and wherein $R_1$ comprises an aryl group;

$R_2$ comprises a group of the formula —$N(R_9R_{10})$, —NHC(O)$R_9$, or —NHC(O)O$R_9$;

wherein $R_9$ and $R_{10}$ independently comprise
1) —H;
2) -Aryl; or
3) a group comprising —$C_{1-6}$ alkyl or —$C_{1-6}$ alkylaryl;

$R_4$ comprises
a) H;
b) -aryl;
c) —$C_{1-6}$ alkyl;
d) —$C_{1-6}$ alkylaryl; or
e) —$C_{1-6}$ alkoxyaryl;

$R_5$, $R_6$, $R_7$, and $R_8$ independently comprise
a) —H;
b) —$C_{1-6}$ alkyl;
c) -aryl;
d) —$C_{1-6}$ alkylaryl;
e) —C(O)—O—$C_{1-6}$ alkyl;
f) —C(O)—O—$C_{1-6}$ alkylaryl;
g) —C(O)—NH—$C_{1-6}$ alkyl;
h) —C(O)—NH—$C_{1-6}$ alkylaryl;
i) —$SO_2$—$C_{1-6}$ alkyl;
j) —$SO_2$—$C_{1-6}$ alkylaryl;
k) —$SO_2$-aryl;
l) —$SO_2$—NH—$C_{1-6}$ alkyl;
m) —$SO_2$—NH—$C_{1-6}$ alkylaryl
n) —C(O)—$C_{1-6}$ alkyl;
o) —C(O)—$C_{1-6}$ alkylaryl;
p) —Y—$C_{1-6}$ alkyl;
q) —Y-aryl;
r) —Y—$C_{1-6}$, alkylaryl;
s) —Y—$C_{1-6}$ alkylene-$NR_{13}R_{14}$; or
t) —Y—$C_{1-6}$ alkylene-W—$R_{15}$;
wherein Y and W independently comprise —$CH_2$—, —O—, —N(H), —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—,

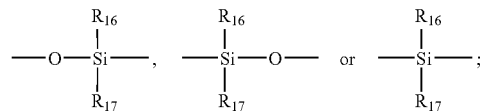

$R_{16}$ and $R_{17}$ independently comprise aryl, $C_1$-$C_6$ alkyl, $C_1$-$C_6$ alkylaryl, $C_1$-$C_6$ alkoxy, or $C_1$-$C_6$ alkoxyaryl;

$R_{15}$ comprises aryl, $C_1$-$C_6$ alkyl, or $C_1$-$C_6$ alkylaryl, or u) halogen, hydroxyl, cyano, carbamoyl, or carboxyl;

$R_{13}$, and $R_{14}$ independently comprise hydrogen, aryl, $C_1$-$C_6$ alkyl, $C_1$-$C_6$ alkylaryl, $C_1$-$C_6$ alkoxy, or $C_1$-$C_6$ alkoxyaryl;

$R_{13}$ and $R_{14}$ may be taken together to form a ring having the formula —$(CH_2)_o$—X—$(CH_2)_p$— bonded to the nitrogen atom to which $R_{13}$ and $R_{14}$ are attached, wherein o and p are, independently, 1, 2, 3, or 4; X comprises a direct bond, —$CH_2$—, —O—, —S—, —$S(O_2)$—, —C(O)—, —CON(H)—, —NHC(O)—, —NHCON(H)—, —$NHSO_2$—, —$SO_2N(H)$—, —C(O)—O—, —O—C(O)—, —$NHSO_2NH$—,

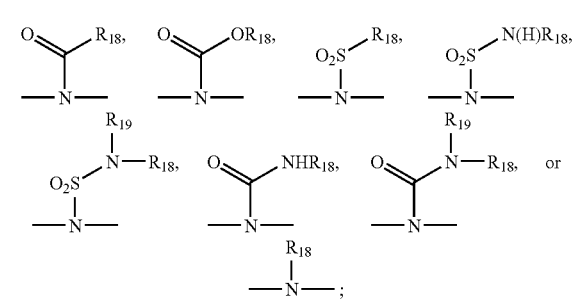

and wherein the aryl and/or alkyl group(s) in $R_4$, $R_5$, $R_6$, $R_7$, $R_8$, $R_9$, $R_{10}$, $R_{13}$, $R_{14}$ $R_{15}$, $R_{16}$, $R_{17}$, $R_{18}$, and $R_{19}$ may be optionally substituted 1-4 times with a substituent group, wherein said substituent group(s) or the term substituted refers to groups comprising:

a) —H;
b) —Z—$C_{1-6}$ alkyl;
—Z-aryl;
—Z—$C_{1-6}$-alkylaryl;
—Z—$C_{1-6}$-alkyl-$NR_{20}R_{21}$; and
—Z—$C_{1-6}$-alkyl-W—$R_{22}$;
 wherein Z and W independently comprise —$CH_2$—, —O—, —N(H), —S—, $SO_2$—, —CON(H)—, —NHC(O)—, —NHCON(H)—, —$NHSO_2$—, —$SO_2N(H)$—, —C(O)—O—, —$NHSO_2NH$—, —O—CO—,

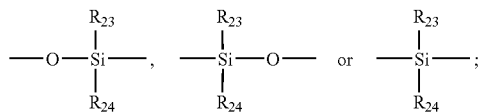

wherein;
$R_{20}$ and $R_{21}$ independently comprise hydrogen, aryl, $C_1$-$C_6$ alkyl, $C_1$-$C_6$ alkylaryl, $C_1$-$C_6$ alkoxy, or $C_1$-$C_6$ alkoxyaryl; and
$R_{22}$, $R_{23}$, and $R_{24}$ independently comprise aryl, $C_1$-$C_6$ alkyl, $C_1$-$C_6$ alkylaryl, $C_1$-$C_6$ alkoxy, or $C_1$-$C_6$ alkoxyaryl; or
c) halogen, hydroxyl, cyano, carbamoyl, or carboxyl; and
$R_{20}$ and $R_{21}$ may be taken together to form a ring having the formula —$(CH_2)_q$—X—$(CH_2)_r$— bonded to the nitrogen atom to which $R_{20}$ and $R_2$ are attached wherein q and r are, independently, 1, 2, 3, or 4; X comprise a direct bond, —$CH_2$—, —O—, —S—, —$S(O_2)$—, —C(O)—, —CON(H)—, —NHC(O)—, —NHCON(H)—, —$NHSO_2$—, —$SO_2N(H)$—, —C(O)—O—, —O—C(O)—, —$NHSO_2NH$—,

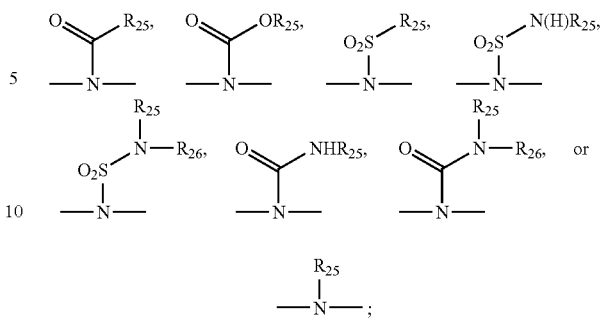

$R_{25}$, $R_{26}$, and $R_{27}$ independently comprise hydrogen, aryl, $C_1$-$C_6$ alkyl, or $C_1$-$C_6$ alkylaryl; or a pharmaceutically acceptable salt, solvate or prodrug thereof.

In the compounds of Formula (I) and (II), the various functional groups represented should be understood to have a point of attachment at the functional group having the hyphen. In other words, in the case of —$C_{1-6}$ alkylaryl, it should be understood that the point of attachment is the alkyl group; an example would be benzyl. In the case of a group such as —C(O)—NH—$C_{1-6}$ alkylaryl, the point of attachment is the carbonyl carbon.

In the above Formula (I), the subscripts m and n indicate the presence of up to 3 methylene linkages; in other words, if m is 3, the $R_1$ group will be bonded via a —$CH_2CH_2CH_2$— linkage. If m is zero, the $R_1$ group will be directly attached, i.e., via a covalent bond.

Also included within the scope of the invention are the individual enantiomers of the compounds represented by Formula (I) above as well as any wholly or partially racemic mixtures thereof. The present invention also covers the individual enantiomers of the compounds represented by the Formula above as mixtures with diastereoisomers thereof in which one or more stereocenters are inverted.

Compounds of the present invention preferred for their high biological activity are listed by name below in Table 1.

TABLE 1

| Example | Structure | Chemical Name |
|---|---|---|
| 1 | 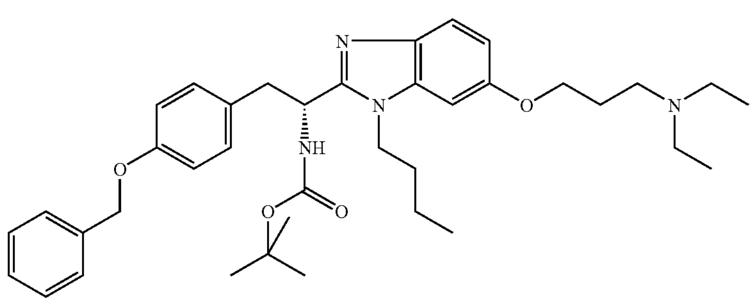 | 2-[(1R)-2-(4-Benzyloxyphenyl)-1-tert-butoxycarbonylamino-1-ethyl]-3-butyl-5-(3-diethylamino-1-propoxy)benzimidazole |

TABLE 1-continued

| Example | Structure | Chemical Name |
| --- | --- | --- |
| 2 | 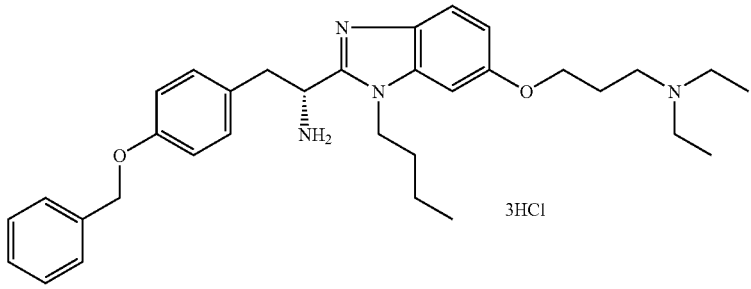 | 2-[(1R)-2-(4-Benzyloxyphenyl)-1-amino-1-ethyl]-3-butyl-5-(3-diethylamino-1-propoxy)benzimidazole Trihydrochloride |
| 3 | 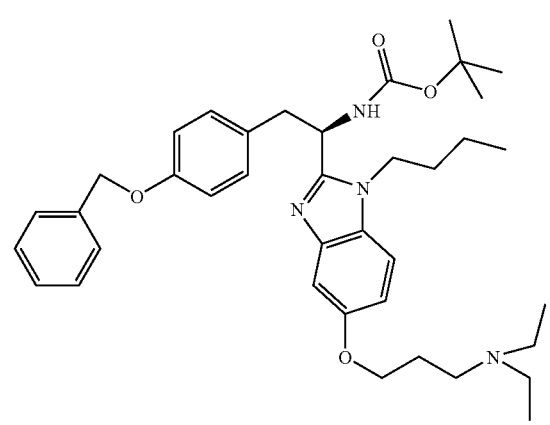 | 2-[(1R)-2-(4-Benzyloxyphenyl)-1-tert-butoxycarbonylamino-1-ethyl]-3-butyl-6-(3-diethylamino-1-propoxy)benzimidazole |
| 4 | 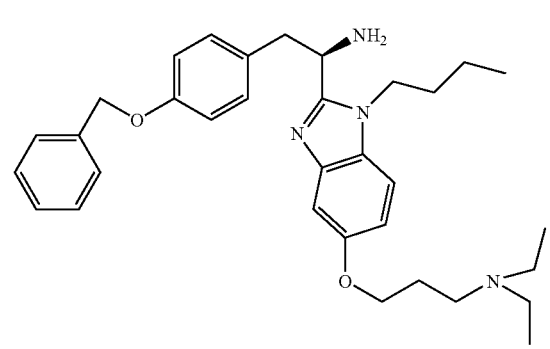 | 2-[(1R)-2-(4-Benzyloxyphenyl)-1-amino-1-ethyl]-3-butyl-6-(3-diethylamino-1-propoxy)benzimidazole |
| 5 | 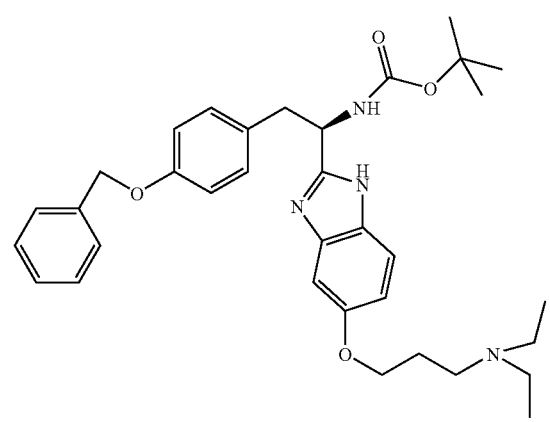 | 2-[(1R)-2-(4-Benzyloxyphenyl)-1-tert-butoxycarbonylamino-1-ethyl]-6-(3-diethylamino-1-propoxy)benzimidazole |

TABLE 1-continued

| Example | Structure | Chemical Name |
| --- | --- | --- |
| 6 | 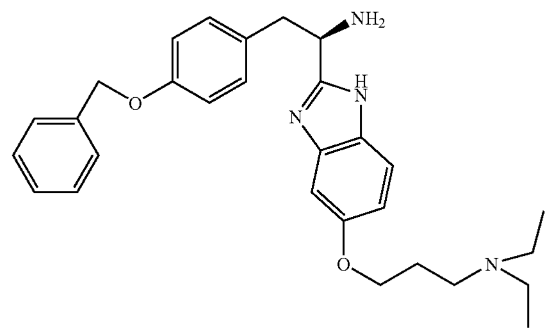 | 2-[(1R)-2-(4-Benzyloxyphenyl)-1-amino-1-ethyl]-6-(3-diethylamino-1-propoxy)benzimidazole |
| 7 | 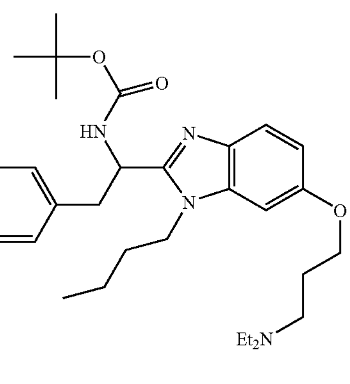 | 2-[2-(3-Benzyloxyphenyl)-1-(tert-butoxycarbonylamino)-1-ethyl]-3-butyl-5-(3-diethylamino-1-propoxy)benzimidazole |
| 8 | 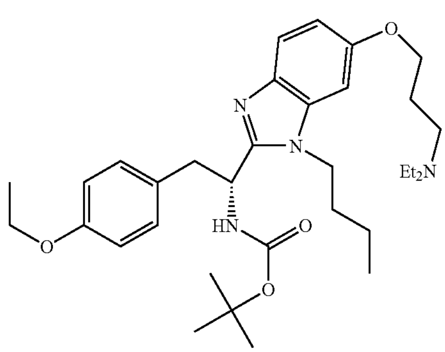 | 2-[(1R)-2-(4-Ethoxyphenyl)-1-(tert-butoxycarbonylamino)-1-ethyl]-3-butyl-5-(3-diethylamino-1-propoxy)benzimidazole |
| 9 | 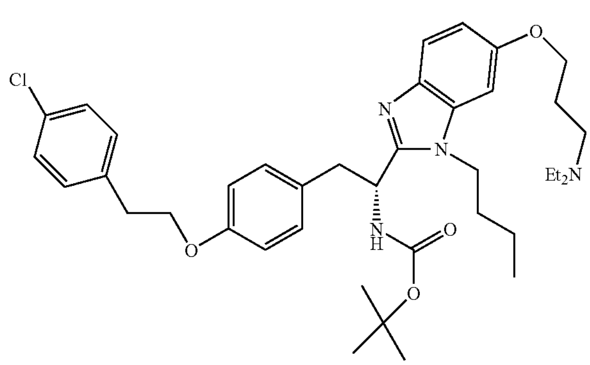 | 2-[(1R)-2-(4-(4-Chloro)phenethoxy)phenyl)-1-(tert-butoxycarbonyl-amino)-1-ethyl]-3-butyl-5-(3-diethylamino-1-propoxy)benzimidazole |

TABLE 1-continued

| Example | Structure | Chemical Name |
| --- | --- | --- |
| 10 | 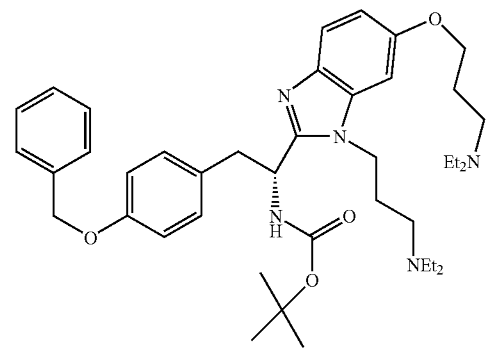 | 2-[(1R)-2-(4-Benzyloxyphenyl)-1-(tert-butoxycarbonylamino)-1-ethyl]-3-(3-diethylamino-1-propyl)-5-(3-diethylamino-1-propoxy)benzimidazole |
| 11 | 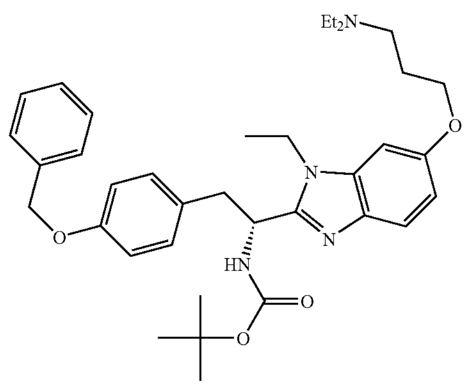 | 2-[(1R)-2-(4-Benzyloxyphenyl)-1-(tert-butoxycarbonylamino)-1-ethyl]-3-ethyl-5-(3-diethylamino-1-propoxy)benzimidazole |
| 12 | 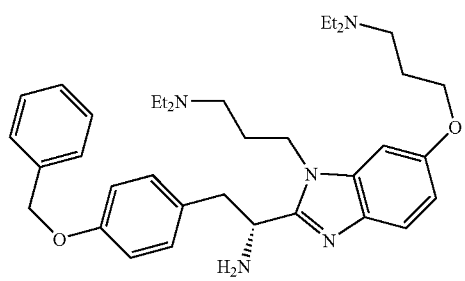 | 2-[(1R)-2-(4-Benzyloxyphenyl)-1-amino-1-ethyl]-3-(3-diethylamino-1-propyl)-5-(3-diethylamino-1-propoxy)benzimidazole |
| 13 | 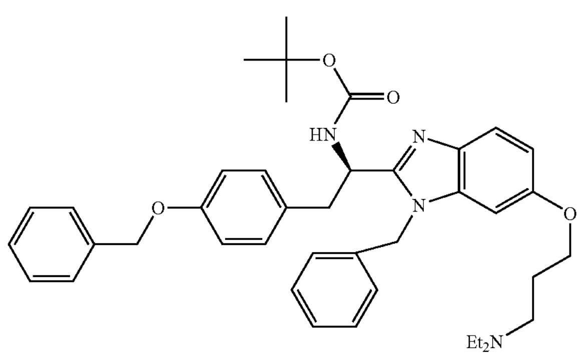 | 2-[(1R)-2-(4-Benzyloxyphenyl)-1-(tert-butoxycarbonylamino)-1-ethyl]-3-benzyl-5-(3-diethylamino-1-propoxy)benzimidazole |

TABLE 1-continued

| Example | Structure | Chemical Name |
|---|---|---|
| 14 | 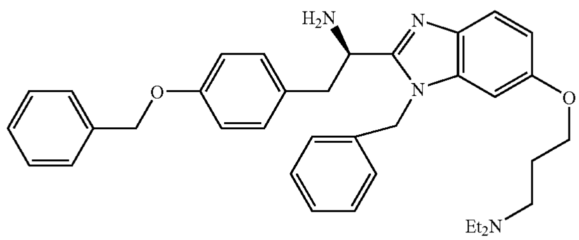 | 2-[(1R)-2-(4-Benzyloxyphenyl)-1-amino-1-ethyl]-3-benzyl-5-(3-diethylamino-1-propoxy)benzimidazole |
| 15 | 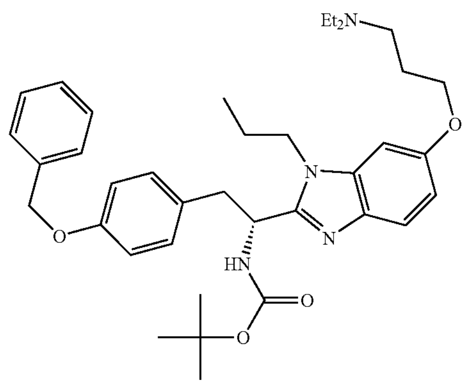 | 2-[(1R)-2-(4-Benzyloxyphenyl)-1-(tert-butoxycarbonylamino)-1-ethyl]-3-propyl-5-(3-diethylamino-1-propoxy)benzimidazole |
| 16 | 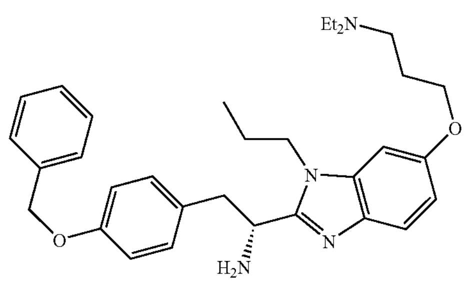 | 2-[(1R)-2-(4-Benzyloxyphenyl)-1-amino-1-ethyl]-3-propyl-5-(3-diethylamino-1-propoxy)benzimidazole |

In another aspect, the present invention comprises a pharmaceutical composition comprising the compound of Formula (I) or Formula (II), and one or more pharmaceutically acceptable carriers, excipients, or diluents.

In an embodiment, the pharmaceutical composition is in the form of an oral dosage or parenteral dosage unit. Preferably, the compound of Formula (I) or Formula (II) is administered as a dose in a range from about 0.01 to 500 mg/kg of body weight per day. More preferably, the compound is administered as a dose in a range from about 0.1 to 200 mg/kg of body weight per day. Even more preferably, the compound is administered as a dose in a range from about 0.1 to 100 mg/kg of body weight per day.

In an embodiment, the pharmaceutical composition further comprises one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

In another aspect, the present invention comprises a method for the inhibition of the interaction of RAGE with its physiological ligands, which comprises administering to a subject in need thereof, at least one compound of Formula (I) or Formula (II).

In an embodiment, the ligand(s) is(are) selected from advanced glycated end products (AGEs), S100/calgranulin/EN-RAGE, β-amyloid and amphoterin.

In yet another aspect, the present invention comprises methods for treating a disease state selected from the group consisting of acute and chronic inflammation, symptoms of diabetes, vascular permeability, nephropathy, atherosclerosis, retinopathy, Alzheimer's disease, erectile dysfunction, and tumor invasion and/or metastasis, which comprises administering to a subject in need thereof a therapeutically effective amount of at least one compound of Formula (I) or Formula (II).

In yet another aspect, the present invention comprises methods for prevention and/or treatment of RAGE mediated human diseases comprising administration to a human in need thereof a therapeutically effective amount of a compound of Formula (I) as claimed in claim 1, wherein a therapeutically effective amount comprises sufficient compound to at least partially inhibit the binding of a ligand to the RAGE receptor.

In an embodiment, the method includes administering to a subject in need thereof at least one adjuvant and/or additional therapeutic agent(s). Preferably, the therapeutic agents are selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

Also preferably, the RAGE mediated human disease comprise acute and/or chronic inflammation, abnormal vascular permeability, nephropathy, atherosclerosis, retinopathy, Alzheimer's disease, erectile dysfunction, tumor invasion and/or metastasis.

As used herein, the term "alkyl" refers to a straight or branched chain hydrocarbon having the number of specified carbon atoms. Examples of "alkyl" as used herein include, but are not limited to, methyl, n-butyl, n-pentyl, isobutyl, and isopropyl, and the like.

As used herein, the term "alkoxy" refers to a straight or branched chain hydrocarbon having the number of specified carbon atoms attached to an oxygen atom. Examples of "alkoxy" as used herein include, but are not limited to, methoxy, n-butoxy, n-pentoxy, isobutoxy, and isopropoxy, and the like.

As used herein, the term "aryl" refers to a five—to seven—membered aromatic ring, or to an optionally substituted benzene ring system, optionally containing one or more nitrogen, oxygen, or sulfur heteroatoms, where N-oxides and sulfur monoxides and sulfur dioxides are permissible substitutions. Such a ring may be fused to one or more five—to seven—membered aromatic rings optionally containing one or more nitrogen, oxygen, or sulfur heteroatoms. Preferred aryl groups include phenyl, biphenyl, 2-naphthyl, 1-naphthyl, phenanthryl, 1-anthracenyl, pyridyl, furyl, furanyl, thiophenyl, indolyl, isothiazolyl, imidazolyl, benzimidazolyl, tetrazolyl, pyrazinyl, pyrimidyl, quinolyl, isoquinolyl, benzofuryl, isobenzofuryl, benzothienyl, benzindoyl, pyrazolyl, isoindolyl, purinyl, carbazolyl, isoxazolyl, thiazolyl, oxazolyl, benzothiazolyl, benzoxazolyl, and the like. In this regard, especially preferred aryl groups include phenyl, 2-naphthyl, 1-naphthyl, biphenyl, and like ring systems optionally substituted by tert-butyloxy, benzyloxy, phenethyloxy, n-butyloxy, ispropyloxy, and phenoxy.

As used herein, the term "alkylene" refers to a straight or branched chain divalent hydrocarbon radical having the specified number of carbon atoms. Examples of "alkylene" as used herein include, but are not limited to, methylene, ethylene, and the like.

As used herein, the term "alkenylene" refers to a straight or branched chain divalent hydrocarbon radical having the specified number of carbon atoms and one or more carbon-carbon double bonds. Examples of "alkenylene" as used herein include, but are not limited to, ethene-1,2-diyl, propene-1,3-diyl, methylene-1,1-diyl, and the like.

As used herein, the term "alkynylene" refers to a straight or branched chain divalent hydrocarbon radical having the specified number of carbon atoms and one or more carbon-carbon triple bonds. Examples of "alkynylene" as used herein include, but are not limited to, ethyne-1,2-diyl, propyne-1,3-diyl, and the like.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the chemical structure terms "contain" or "containing" refer to in-line substitutions at any position along the above defined substituent at one or more of any of O, S, SO, $SO_2$, N, or N-alkyl, including, for example, $-CH_2-O-CH_2-$, $-CH_2-SO_2-CH_2-$, $-CH_2-NH-CH_3$ and so forth.

As used herein, the term "solvate" is a complex of variable stoichiometry formed by a solute (in this invention, a compound of Formula (I)) and a solvent. Such solvents for the purpose of the invention may not interfere with the biological activity of the solute. Solvents may be, by way of example, water, ethanol, or acetic acid.

As used herein, the term "biohydrolyzable ester" is an ester of a drug substance (in this invention, a compound of Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters (e.g., $C_1$-$C_4$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of Formula (I): for example, the lactam formed by a carboxylic group in $R_2$ and an amine in $R_4$, and b) compounds which may be oxidized or reduced biologically at a given functional group to yield drug substances of Formula (I). Examples of these functional groups include, but are not limited to, 1,4-dihydropyridine, N-alkylcarbonyl-1,4-dihydropyridine, 1,4-cyclohexadiene, tert-butyl, and the like. The term "pharmacologically effective amount" shall mean that amount of a drug or pharmaceutical agent that will elicit the biological or medical response of a tissue, animal or human that is being sought by a researcher or clinician. This amount can be a therapeutically effective amount.

Whenever the terms "alkyl" or "aryl" or either of their prefix roots appear in a name of a substituent (e.g. arylalkoxyaryloxy) they shall be interpreted as including those limitations given above for "alkyl" and "aryl". Alkyl substituents shall be recognized as being functionally equivalent to those having one or more degrees of unsaturation. Designated numbers of carbon atoms (e.g. $C_{1-6}$) shall refer independently to the number of carbon atoms in an alkyl moiety or to the alkyl portion of a larger substituent in which the term "alkyl" appears as its prefix root. Similarly, the term "$C_2$-$C_8$ alkenyl" and $C_2$-$C_8$ alkynyl" refer to groups having from 2 to 8 carbon atoms and at least one carbon-carbon double bond or carbon-carbon triple bond, respectively.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —SO$_2$NH$_2$.

As used herein, the term "carbamoyl" shall refer to the substituent —C(O)NH$_2$.

The present invention also provides methods for the synthesis of compounds useful as intermediates in the preparation of compounds of Formula (I) along with methods for the preparation of compounds of Formula (I).

For example, an aldehyde (1) may be condensed with a phenylenediamine compound (2) in a solvent such as ethanol at a temperature of from 25 to 100 degrees Celsuis, to obtain the product benzimidazole (3), where the intermediate adduct undergoes spontaneous oxidation (Scheme 1).

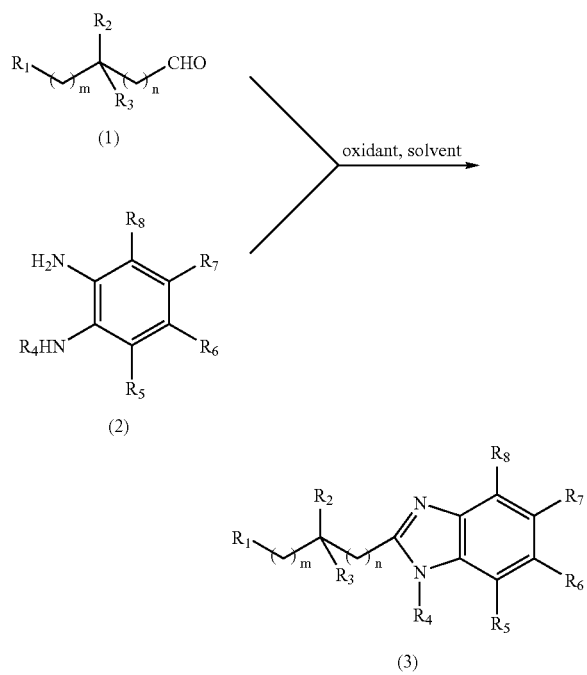

In another embodiment, the aldehyde (1) (Scheme 2) may be synthesized by treatment of the acid (4) with isobutyl chloroformate in the presence of a base such as NMM, in a solvent such as THF, followed by treatment with N-methyl-O-methyldroxylamine, to form the intermediate O,N-dimethylamide. The amide may be isolated, and treated with LAH in THF or ether at 0° C. to afford the aldehyde (1). Alternately, the aldehyde (1) may be synthesized by treatment of the acid (4) with isobutyl chloroformate in the presence of a base such as NMM, in a solvent such as THF, followed by treatment with sodium borohydride to give the primary alcohol as an intermediate. The alcohol may be oxidized with a reagent such as DMSO/oxalyl chloride, followed by treatment with triethylamine, in DCM at −78° C. to 0° C., to give the aldehyde (1). Alternately, the alcohol intermediate may be oxidized by treatment with pyridinium dichromate in DCM at a temperature of from 0° C. to 25° C., to afford the aldehyde (1).

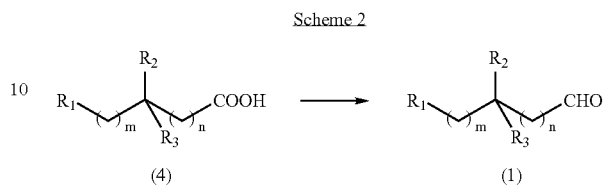

Scheme 3 describes the synthesis of substituted arylenediamines.

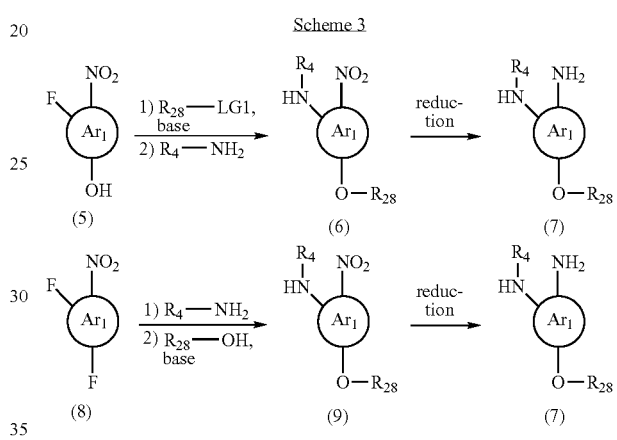

Thus, in an embodiment, an ortho-fluoro nitrophenol such as (5) may be alkylated with an alkyl halide or other alkylating agent $R_{28}$-$LG_1$, in the presence of an alkali metal carbonate as base in a solvent such as DMF or acetonitrile. $LG_1$ may represent a nucleofugal group such as iodide, bromide, methanesulfonate, and the like. In this transformation, $R_{28}$ is alkyl or a group capable of undergoing nucleophilic displacement at the carbon bearing $LG_1$. The intermediate may be treated with with an amine $R_4$—NH$_2$ in the presence of a tertiary amine base, in a solvent such as THF, at a temperature of from 0° C. to 100° C., to afford (6). Reduction of the nitro group in (6) may be accomplished by treatment of (6) in neutral or acidic ethanol with stannous chloride at a temperature of from 25° C. to 100° C. to afford the aniline (7). Alternately, (6) may be reduced by treatment of (6) with a noble metal catalyst such as palladium on charcoal and a hydrogen source such as gaseous hydrogen or ammonium formate, in a solvent such as ethanol, at a temperature of from 25° C. to 80° C., to afford (7). The difluoronitroaromatic compound (8) may be employed in similar manner, where in (8), one fluoro is ortho to the nitro group. Treatment of (8) with the one equivalent of amine $R_4$—NH$_2$ gives preferential substitution of the ortho fluorine. The second fluorine in the intermediate may be substituted by an alcohol $R_{28}$—OH to afford (9). In this instance, $R_{28}$ may be alkyl or aryl. Reduction of the nitro group in (9) as before with stannous chloride provides (7).

Scheme 4 describes the synthesis of phenyl ethers (11).

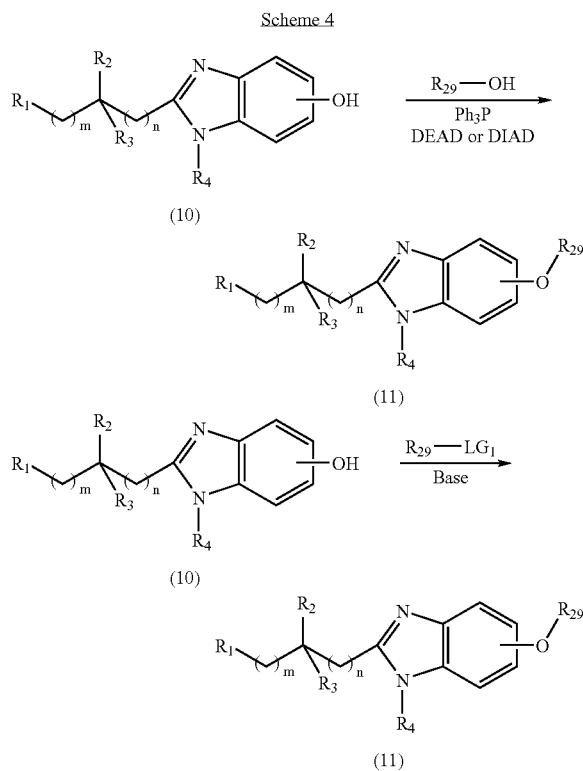

Thus, in an embodiment, a phenol (10) may be treated with an alcohol $R_{29}$—OH, triphenylphosphine or other suitable phosphine reagent, and diethyl azodicarboxylate (DEAD) or diisopropyl azodicarboxylate (DIAD), in a solvent such as THF at a temperature of from −70° C. to 25° C. to give (11). $R_{29}$ is an alkyl group, preferentially primary or secondary in nature. Alternately, (10) may be treated with $R_{29}$-$LG_1$ in the presence of an alkali metal carbonate or other suitable base, in a solvent such as DMF, acetone, or acetonitrile, at a temperature of from 25° C. to 100° C., to provide (11).

Described below are general procedures used in the methods of the present invention.

General Experimental

LC-MS data was obtained using gradient elution on a Waters 600 controller equipped with a 2487 dual wavelength detector and a Leap Technologies HTS PAL Autosampler using an YMC Combiscreen ODS-A 50×4.6 mm column. A three minute gradient was run from 25% B (97.5% acetonitrile, 2.5% water, 0.05% TFA) and 75% A (97.5% water, 2.5% acetonitrile, 0.05% TFA) to 100% B. The MS was a Micromass ZMD instrument. All data was obtained in the positive mode unless otherwise noted. $^1$H NMR data was obtained on a Varian 300 MHz spectrometer.

Abbreviations used in the Examples are as follows:
APCI=atmospheric pressure chemical ionization
BOC=tert-butoxycarbonyl
BOP=(1-benzotriazolyloxy)tris(dimethylamino)phosphonium hexafluorophosphate d=day
DIAD=diisopropyl azodicarboxylate
DCC=dicyclohexylcarbodiimide
DCM=dichloromethane
DIEA=diisopropylethylamine
DMF=N,N-dimethylformamide
DMPU=1,3-dimethypropylene urea
DMSO=dimethylsulfoxide
EDC=1-ethyl-3-(3-dimethyla minopropyl)-carbod iimide hydrochloride
EDTA=ethylenediamine tetraacetic acid
ELISA=enzyme—linked immunosorbent assay
ESI=electrospray ionization
ether=diethyl ether
EtOAc=ethyl acetate
FBS=fetal bovine serum
g=gram
h=hour
HBTU=O-benzotriazol-1-yl-N,N,N',N'-tetramethyluronium hexafluorophosphate
HMPA=hexamethylphosphoric triamide
HOBt=1-hydroxybenzotriazole
Hz=hertz
i.v.=intravenous
kD=kiloDalton
L=liter
LAH=lithium aluminum hydride
LDA=lithium diisopropylamide
LPS=lipopolysaccharide
M=molar
m/z=mass to charge ratio
mbar=millibar
MeOH=methanol
mg=milligram
min=minute
mL=milliliter
mM=millimolar
mmol=millimole
mol=mole
mp=melting point
MS=mass spectrometry
N=normal
NMM=N-methylmorpholine, 4-methylmorpholine
NMR=nuclear magnetic resonance spectroscopy
p.o.=per oral
PBS=phosphate buffered saline solution
PMA=phorbol myristate acetate
ppm=parts per million
psi=pounds per square inch
$R_f$=relative TLC mobility
rt=room temperature
s.c.=subcutaneous
SPA=scintillation proximity assay
TEA=triethylamine
TFA=trifluoroacetic acid
THF=tetrahydrofuran
THP=tetrahydropyranyl
TLC=thin layer chromatography
$T_r$=retention time Thus, in an embodiment, the following compounds were synthesized according to the Schemes described herein.

General Procedures

General Procedure I: Synthesis of Substituted Aldehydes:
Step A: A solution of substituted acid in $CH_2Cl_2$ (0.05-1 M) is cooled to −15° C. and treated with NMM (1-2 eq) and isobutyl chloroformate (1-2 eq). The resulting reaction mixture is stirred for 15 min at −15° C. and treated with solid N,O-dimethylhrdoxylamine hydrochloride (1-2 eq). Then the reaction mixture is allowed to warm up to rt gradually and stirring continued for another 45 min. The reaction mixture was diluted with DCM and washed with water and brine. The solution is then dried and the solvent is removed in vacuo to afford the crude amide.

Step B: The crude amide is dissolved in diethyl ether (0.05-1 M) and cooled to −20° C. A 1 M solution of lithium aluminum hydride in THF (0.5-1 eq) is slowly added to the reaction mixture and the stirring is continued for 0.5-1 h at −20° C. Then methanol (1 mL) is added to the reaction mixture at −20° C. The reaction mixture is allowed to warm up to 0° C. and treated with 10% aq. potassium bisulfate. The resulting mixture is poured into a separatory funnel and extracted with ethyl acetate. The organic layer is washed with 0.5 N HCl, water, and brine. The extract is then dried and the solvent is removed in vacuo to afford the crude aldehyde.

General Procedure II: Synthesis of Hydroxy-Substituted Phenylenediamines

Step A: A 2-fluoronitroaromatic compound is dissolved in THF (0.05-1 M) and is treated with a primary amine (1-2 eq) and refluxed for 6 h. The reaction mixture is cooled to rt and concentrated in vacuo. The residue is redissolved in EtOAc. The mixture is washed with saturated sodium bicarbonate solution, water, and brine. The organic phase is then dried over sodium sulfate and the solvent is removed in vacuo to afford the amine.

Step B: The 2-alkylaminonitroaromatic compound obtained as above is dissolved in ethanol (0.05-1 M) and treated with tin (II) chloride dihydrate (2-10 eq). The contents are then refluxed overnight. The reaction mixture is then cooled to rt and treated with saturated sodium bicarbonate solution with stirring until the pH of the reaction mixture is 7-8. The precipitate formed is filtered off and the filtrate is concentrated to about ⅓ volume and diluted with ethyl acetate. The organic layer is washed with brine and dried over sodium sulfate. Solvent removal in vacuo affords the aniline.

General Procedure III: Synthesis of Alkoxy-Substituted Phenylenediamines

Step A: A 2-fluoro-4-hydroxynitroaromatic compound is dissolved in DMF (0.05-1 M) and is treated with an alkyl halide or methanesulfonate (1.2-1.5 eq) and $K_2CO_3$ or $Cs_2CO_3$ (2 eq) and heated at 70-90° C. for 6-12 h. The reaction mixture is cooled to rt and diluted with water to afford a homogenous mixture. The solution is extracted with EtOAc twice. The combined organics is washed with water, and brine. The organic phase is then dried over sodium sulfate and the solvent is removed in vacuo to afford the 4-alkoxynitroaromatic compound.

Step B: The 4-alkoxynitroaromatic compound obtained as above is dissolved in THF (0.05-1 M) and is treated with a primary amine (1-2 eq) at rt. After completion of the reaction, the reaction mixture is concentrated in vacuo. The residue is redissolved in EtOAc. The mixture is washed with saturated sodium bicarbonate solution, water, and brine. The organic phase is then dried over sodium sulfate and the solvent is removed in vacuo to afford the nitroamine.

Step C: The nitroamine compound is dissolved in ethanol (0.05-1M) and is added with 10% Pd/C (100 mg/mmol). The reaction mixture is hydrogenated at rt under 1atm pressure. The contents are filtered through a Celite pad and the solvent is removed in vacuo to afford the diamine.

Alternatively, the nitroamine compound is reduced with tin (II) chloride as described in the general procedure II (Step B).

General Procedure IV: Synthesis of 2-Substituted Benzimidazoles

Ortho-phenylenediamine compound and aldehyde compound (approx equimolar amounts of each) are mixed in ethanol (0.05-2 M) and the solution is refluxed overnight. The contents are then cooled to rt and concentrated in vacuo. The residue obtained was purified by silica gel column chromatography eluting with 5% methanol/chloroform to afford the desired benzimidazole product.

General Procedure V: Alkylation of Phenol

A phenol is stirred in dry THF (0.05-1 M) and treated with an alcohol (1-2 eq) and triphenylphosphine (1-2 eq). The mixture is cooled to 0° C. and treated with diisopropyl azodicarboxylate (DIAD) or diethyl azodicarboxylate (DEAD) (1-2 eq). The reaction mixture is allowed to warm up to rt and stirred under nitrogen atmosphere overnight. The reaction mixture is diluted with water and the mixture is extracted with EtOAc. The organic layers are washed with water and brine and dried over $Na_2SO_4$. The solvent is removed in vacuo and the resulting product was purified by silica gel column chromatography to afford the alkylated phenol.

EXAMPLE 1

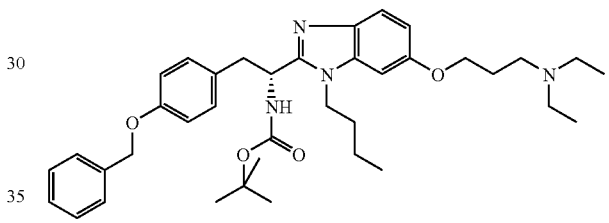

A solution of BOC-D-(O-benzyl)tyrosine (557 mg) in $CH_2Cl_2$ (10 mL) is cooled to −15° C. and treated with N-methylmorpholine (0.5 mL) and isobutyl chloroformate (0.3 mL). The resulting reaction mixture is stirred for 15 min at −15° C. and treated with solid N,O-dimethylhydroxylamine hydrochloride (300 mg). Then the reaction mixture is allowed to warm up to room temperature gradually and stirring continued for another 45 min. The reaction mixture was diluted with $CH_2Cl_2$ (10 mL), washed with water (15 mL) and brine (15 mL). The solution is then dried over sodium sulfate, filtered and the solvent is removed in vacuo to afford the crude amide (760 mg) which was used for the next step without further purification.

The crude amide from above is dissolved in diethyl ether (5 mL) and cooled to −20° C. A 1 M solution of lithium aluminum hydride in THF (4 mL) is slowly added to the reaction mixture and the stirring is continued for 45 min at −20° C. Then methanol (1 mL) is added to the reaction mixture at −20° C. The reaction mixture is allowed to warm up to 0° C. and treated with 10% aq. potassium bisulfate solution (10 mL). The resulting mixture is poured into a separatory funnel and extracted with ethyl acetate (2×10 mL) and layers separated. The organic layer is washed with 0.5 N HCl (20 mL), water (20 mL) and brine (20 mL). The extract is then dried over sodium sulfate, filtered and the solvent is removed in vacuo to afford the crude aldehyde (520 mg) which was used without further purification.

3-Fluoro-4-nitrophenol (800 mg) is dissolved in THF (10 mL) and added with n-butylamine (1 mL) and refluxed for 6 h. The reaction mixture is cooled to room temperature and concentrated in vacuo. The residue is redissolved in ethyl acetate (25 mL) and taken up in separatory funnel. The contents are washed with saturated sodium bicarbonate solution (20 mL), water (20 mL) and brine (20 mL). The extract is then dried over sodium sulfate, filtered and the solvent is removed in vacuo to afford the crude amine (950 mg) which was used without further purification.

3-n-Butylamino-4-nitrophenol (450 mg) obtained as above is dissolved in ethanol (10 mL) and treated with tin (II) chloride dihydrate (3 g). The contents are then refluxed overnight. The reaction mixture is then cooled to room temperature and added with saturated sodium bicarbonate solution with stirring until the pH of the reaction mixture is 7-8. The precipitate formed is filtered off and the filtrate is concentrated to about ⅓ of the original volume and diluted with ethyl acetate (20) and the layers separated. The organic layer is washed with brine (10 mL) and dried over sodium sulfate. Filtration and solvent removal in vacuo affords the crude aniline (300 mg) which was used without further purification.

260 mg of the diaminophenol and 355 mg of the amino aldehyde obtained above from BOC-D-(O-benzyl)tyrosine is dissolved in ethanol (10 mL) and the solution is refluxed overnight. The contents are then cooled to room temperature and concentrated in vacuo. The residue obtained was passed through a column of silica gel and eluted with 5% methanol/chloroform to afford 240 mg of the desired benzimidazole product.

170 mg of the benzimidazole product formed above is dissolved in dry THF (5 mL) and added with 3-diethylamino-1-propanol (150 µL) and triphenylphosphine (262 mg). The contents are cooled to 0° C. and added with diisopropyl azodicarboxylate (200 µL). The reaction mixture is allowed to warm up to room temperature and stirred under nitrogen atmosphere overnight. The reaction mixture is diluted with ethyl acetate/water (5 mL/3 mL) and the layers separated. The aqueous layer is further extracted with ethyl acetate (5 mL). The organic layers are combined and washed with water and brine and dried over $Na_2SO_4$. The solution is filtered and the solvent is removed in vacuo. The resulting crude product was purified by silica gel column chromatography using triethylamine/methanol/$CHCl_3$/hexane (1:2:40:40) as eluent to afford 120 mg of Example 1. LC: Tr 1.84 min; MS: m/z 629.4 (M+1)

EXAMPLE 2

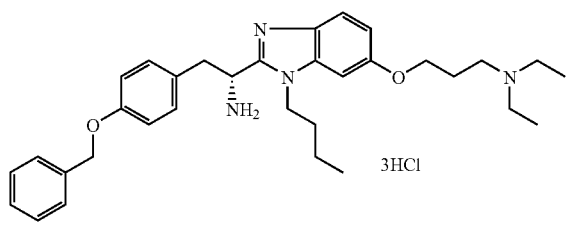

3HCl 40 mg of the Example 1 is stirred in 4 M HCl in dioxane (1 mL) overnight. Solvent is then removed in vacuo and the residue obtained is triturated with ether and stirred. The ether is decanted off and the ether wash is repeated twice more. The product is then dried under-vacuum to afford the amine salt Example 2 as a pale yellow solid (30 mg). LC: Tr 1.65 min; MS: m/z 529.4 (M+H).

EXAMPLE 3

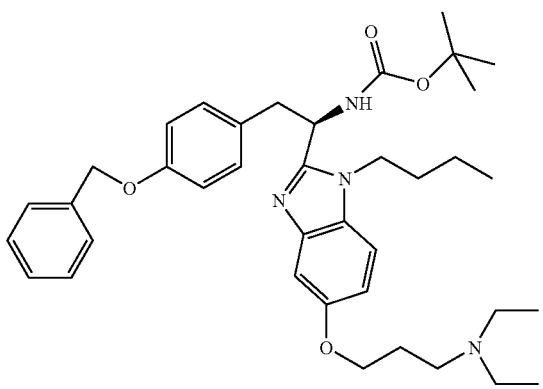

MsCl (6.0 mmol) was added dropwise at 0° C. to a stirred solution of 3-diethylamino-1-propanol (6.0 mmol), TEA (6.0 mmol) in anhydrous DCM (6 mL), and the mixture was stirred at the same temperature for 10 min, and at room temperature for additional 1 h. After the removal of the solvent in vacuo, the solid residue was mixed with 4-chloro-3-nitrophenol (5.0 mmol), and $K_2CO_3$ (10 mmol) in anhydrous DMF (10 mL), following the general procedure III (Step A). The crude product is purified using silica gel column chromatography 5% MeOH/DCM as eluent to yield 2-chloro-5-(3-diethylamino-1-propoxy)nitrobenzene (1.3 g).

The alkoxynitro compound (1 mmol) obtained as above is added with n-butylamine (2 mL) and copper (I) chloride (1 mmol) in a sealed tube and heated at 80° C. overnight. The reaction mixture is cooled to rt, diluted with water (10 mL) and extracted with EtOAc (2×10 mL). The combined organic layers are then washed with water and brine and dried over Na2SO4. Removal of the solvent in vacuo yielded the product, 2-n-butylamino-5-(3-diethylamino-1-propoxy)nitrobenzene (300 mg) which is used for further transformation without any purification.

The nitroamine obtained as above (0.8 mmol) is dissolved in EtOH (5 mL) and added with 10% Pd/C (80 mg). The reaction mixture is hydrogenated as in the general procedure III (Step C) to obtain the product, 2-n-butylamino-5-(3-diethylamino-1-propoxy)aniline (200 mg).

A mixture of the diamine formed as above (0.5 mmol) and the aldehyde (0.5 mmol) obtained from the reduction of BOC-D-(O-benzyl)tyrosine (as described in example 1) are used according to the general procedure IV to afford the product, 2-[(1R)-2-(4-Benzyloxyphenyl)-1-tert-butoxycarbonylamino-1-ethyl]-3-butyl-6-(3-diethylamino-1-propoxy)benzimidazole (100 mg). LC: Tr 2.15 min; MS: m/z 629.7 (M+H).

EXAMPLE 4

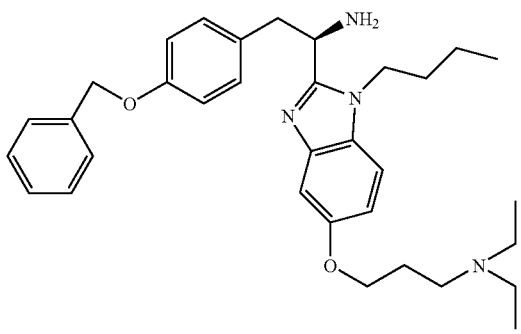

40 mg of the Example 3 is stirred in 4 M HCl in dioxane (1 mL) overnight. Solvent is then removed in vacuo and the residue obtained is triturated with ether and stirred. The ether is decanted off and the ether wash is repeated twice more. The product is then dried under vacuum to afford the amine 2-[(1R)-2-(4-Benzyloxyphenyl)-1-amino-1-ethyl]-3-butyl-6-(3-diethylamino-1-propoxy)benzimidazole as hydrochloride salt (30 mg). LC: Tr 2.02 min; MS: m/z 529.7 (M+H).

EXAMPLE 5

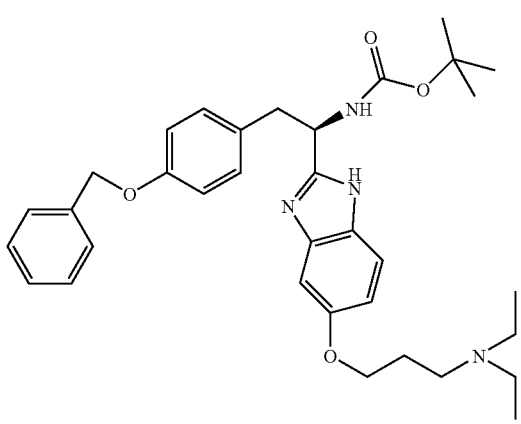

A solution of 3-fluoro-4-nitrophenol (2 mmol) and methanesulfonate of 3-diethylamino-1-propanol (2.5 mmol) in DMF (4 mL) is added with K2CO3 (4 mmol) and heated following the general procedure III (Step A). The product, 2-fluoro-4-(3-diethylamino-1-propoxy)nitrobenzene is obtained (470 mg) after purification using silica gel column chromatography.

The nitro compound obtained as above (1.5 mmol) is dissolved in DMF (4 mL) and added with ammonium carbonate (500 mg). The reaction mixture is then heated at 80° C. for 48 h. EtOAc (2×10 mL). The combined organic layers are then washed with water and brine and dried over Na₂SO₄. Removal of the solvent in vacuo yielded the 2-nitro-5-(3-diethylamino-1-propoxy)aniline (300 mg) which is used for further transformation without any purification.

The nitroaniline obtained as above (0.8 mmol) is dissolved in EtOH (5 mL) and added with 10% Pd/C (80 mg). The reaction mixture is hydrogenated as in the general procedure III (Step C) to obtain the product, 2-amino-4-(3-diethylamino-1-propoxy)aniline (200 mg).

A mixture of the diamine formed as above (0.5 mmol) and the aldehyde (0.5 mmol) obtained from the reduction of BOC-D-(O-benzyl)tyrosine (as described in example 1) are used according to the general procedure IV to afford the product, 2-[(1R)-2-(4-Benzyloxyphenyl)-1-tert-butoxycarbonylamino-1-ethyl]-6-(3-diethylamino-1-propoxy)benzimidazole (90 mg). LC: Tr 1.91 min; MS: m/z 573.6 (M+H).

EXAMPLE 6

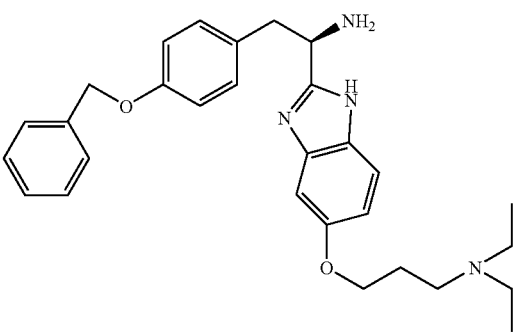

30 mg of the Example 3 is stirred in 4 M HCl in dioxane (1 mL) overnight. Solvent is then removed in vacuo and the residue obtained is triturated with ether and stirred. The ether is decanted off and the ether wash is repeated twice more. The product is then dried under vacuum to afford the 2-[(1R)-2-(4-Benzyloxyphenyl)-1-amino-1-ethyl]-6-(3-diethylamino-1-propoxy)benzimidazole as hydrochloride salt (20 mg). LC: Tr 1.80 min; MS: m/z 473.6 (M+H).

EXAMPLE 7

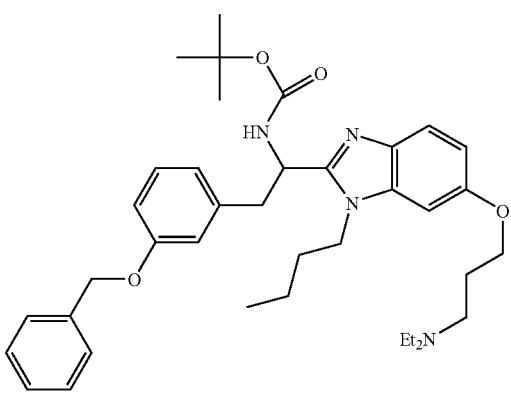

A solution Boc-3-Tyr-OH (4.2 mmol) and benzyl bromide (10 mmol) in DMF (20 ml) is treated with K₂CO₃ (20 mmole) and stirred at room temperature for 20 h. The reaction mixture is diluted with ether (150 ml) and the contents are washed with water (2×100 ml) and brine (1×50 ml) and dried over Na₂SO₄. After removal of the solvent a pale yellow oil is obtained which is dissolved in THF (20 mL). 2N aq. NaOH (20 ml) is added to the reaction mixture and stirred overnight. After completion of the reaction, ether (100 ml) and water (50 ml) are added and stirred vigorously. The ether layer was discarded and the aqueous layer was made acidic by addition of citric acid, the product was extracted with ether (3×40 ml) and dried (Na$_2$SO$_4$). Removal of the solvent in vacuo yielded the product, Boc-(O-benzyl)-3-Tyr-OH (1.6 g) as white solid.

A solution of Boc-(O-benzyl)-3-Tyr-OH (600 mg) in CH$_2$Cl$_2$ (10 mL) is cooled to −15° C. and treated with N-methylmorpholine (0.5 mL) and isobutyl chloroformate (0.3 mL). The resulting reaction mixture is stirred for 15 min at −15° C. and treated with solid N,O-dimethylhydroxylamine hydrochloride (300 mg). The rest of the procedure is as described in example 1. The crude amide (730 mg) obtained was used for the next step without further purification.

The crude amide from above is in diethyl ether (5 mL) is converted to the corresponding aldehyde using 1 M solution of lithium aluminum hydride in THF (4 mL) following the procedure described in example 1. The crude aldehyde (500 mg) was used without further purification.

A solution of 2-fluoro-4-(3-diethylamino-1-propoxy)nitrobenzene (2 mmol; preparation described in Example 5) in THF (5 mL) is treated with n-butylamine (2.4 eq) at rt. After completion of the reaction, the reaction mixture is concentrated in vacuo. The residue is redissolved in EtOAc (10 mL), washed with saturated sodium bicarbonate solution, water, and brine. The organic phase is then dried over sodium sulfate and the solvent is removed in vacuo to afford the product, 2-n-butylamino-4-(3-diethylamino-1-propoxy)nitrobenzene (580 mg) which was used for further transformation without any purification.

The nitroamine obtained as above (1.0 mmol) is dissolved in EtOH (5 mL) and added with 10% Pd/C (100 mg). The reaction mixture is hydrogenated as in the general procedure III (Step C) to obtain the product, 2-n-butylamino-4-(3-diethylamino-1-propoxy)aniline (260 mg).

A mixture of the diamine formed as above (0.5 mmol) and the aldehyde (0.5 mmol) obtained from the reduction of BOC-(O-benzyl)-3-Tyr-OH (described earlier) are used according to the general procedure IV to afford the product, 2-[2-(3-Benzyloxyphenyl)-1-(tert-butoxycarbonylamino)-1-ethyl]-3-butyl-5-(3-diethylamino-1-propoxy)benzimidazole (130 mg). LC: Tr 2.12 min; MS: m/z 630.0 (M+H).

EXAMPLE 8

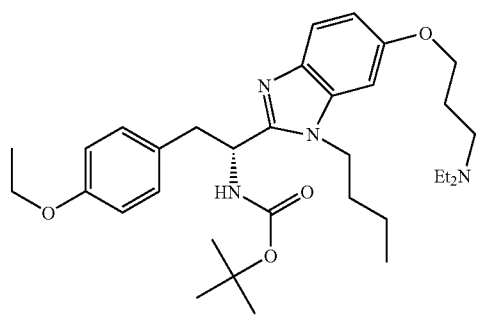

A solution of Boc-(OEt)-Tyr-OH (2 mmol) in CH$_2$Cl$_2$ (10 mL) is cooled to −15° C. and treated with N-methylmorpholine (0.5 mL) and isobutyl chloroformate (0.3 mL). The resulting reaction mixture is stirred for 15 min at −15° C. and treated with solid N,O-dimethylhydroxylamine hydrochloride (300 mg). The rest of the procedure is as described in example 1. The crude amide (700 mg) obtained was used for the next step without further purification.

The crude amide from above is in diethyl ether (5 mL) is converted to the corresponding aldehyde using 1 M solution of lithium aluminum hydride in THF (4 mL) following the procedure described in example 1. The crude aldehyde (500 mg) was used without further purification.

A mixture of the aldehyde formed as above (0.5 mmol) and 2-n-butylamino-4-(3-diethylamino-1-propoxy)aniline (0.5 mmol; synthesis described in example 7) is used according to the general procedure IV to afford the product, 2-[(1R)-2-(4-Ethoxyphenyl)-1-(tert-butoxycarbonylamino)-1-ethyl]-3-butyl-5-(3-diethylamino-1-propoxy)benzimidazole (120 mg). LC: Tr 1.98 min; MS: m/z 568.0 (M+H).

EXAMPLE 9

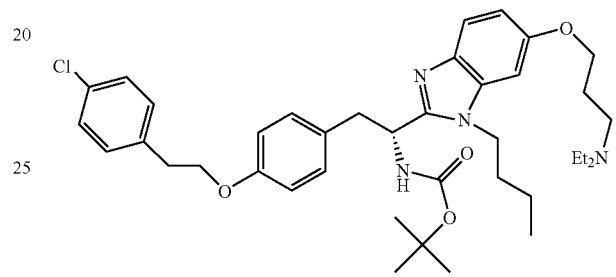

A solution of Boc-D-Tyr-OH (2 mmol) and benzyl bromide (2.4 mmol) in DMF (10 mL) was added with DIEA (3 mmol) and stirred at rt. After the completion of the reaction, 4-chlorophenethyl alcohol (2.2 mmol) was added to the reaction mixture followed by triphenyl phosphine (2.2 mmol) and DIAD (2.4 mmol). The work-up is as described in general procedure V. The crude product, is purified by silica gel column chromatography to afford Boc-D-(O-4-chlorophenethyl)-Tyr-OBn (800 mg).

The benzyl ester formed above (1 mmol) is dissolved in ethyl acetate (10 mL) and treated with 5% Pd/C. The reaction mixture is hydrogenated at 1 atm for 10-20 min. The product formed, Boc-D-(O-4-chlorophenethyl)-Tyr-OH (360 mg) is used for further transformation without any purification.

A solution Boc-D-(O-4-chlorophenethyl)-Tyr-OH (1 mmol) in CH$_2$Cl$_2$ (10 mL) is cooled to −15° C. and treated with N-methylmorpholine (0.5 mL) and isobutyl chloroformate (0.3 mL). The resulting reaction mixture is stirred for 15 min at −15° C. and treated with solid N,O-dimethylhydroxylamine hydrochloride (300 mg). The rest of the procedure is as described in example 1. The crude amide (400 mg) obtained was used for the next step without further purification.

The crude amide from above is in diethyl ether (5 mL) is converted to the corresponding aldehyde using 1 M solution of lithium aluminum hydride in THF (4 mL) following the procedure described in example 1. The crude aldehyde (300 mg) was used without further purification.

A mixture of the aldehyde formed as above (0.5 mmol) and 2-n-butylamino-4-(3-diethylamino-1-propoxy)aniline (0.5 mmol; synthesis described in example 7) is used according to the general procedure IV to afford the product, 2-[(1R)-2-(4-(4-Chloro)phenethoxy) phenyl]-1-(tert-butoxycarbonylamino)-1-ethyl]-3-butyl-5-(3-diethylamino-1-propoxy)benzimidazole (150 mg). LC: Tr 2.24 min; MS: m/z 678.0 (M+H).

EXAMPLE 10

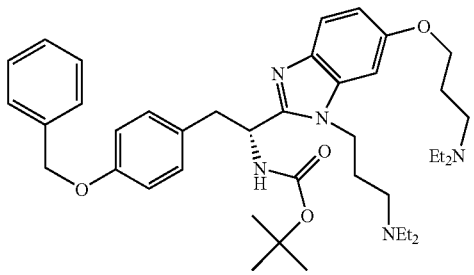

A solution of 2-fluoro-4-(3-diethylamino-1-propoxy)nitrobenzene (2 mmol; preparation described in Example 5) in THF (5 mL) is treated with 3-diethylamino-1-propylamine (2.4 mmol at rt. After completion of the reaction, the reaction mixture is concentrated in vacuo. The residue is redissolved in EtOAc (10 mL), washed with saturated sodium bicarbonate solution, water, and brine. The organic phase is then dried over sodium sulfate and the solvent is removed in vacuo to afford the product, 2-(3-diethylamino-1-propylamino)-4-(3-diethylamino-1-propoxy)nitrobenzene (620 mg) which was used for further transformation without further purification.

The nitroamine obtained as above (1.0 mmol) is dissolved in EtOH (5 mL) and added with 10% Pd/C (100 mg). The reaction mixture is hydrogenated as in the general procedure III (Step C) to obtain the product, 2-(3-diethylamino-1-propylamino)-4-(3-diethylamino-1-propoxy)aniline (300 mg).

A mixture of the diamine formed as above (0.5 mmol) and the aldehyde (0.5 mmol) obtained from the reduction of BOC-(O-benzyl)-Tyr-OH (described earlier) are used according to the general procedure IV to afford the product, 2-[(1R)-2-(4-Benzyloxyphenyl)-1-(tert-butoxycarbonylamino)-1-ethyl]-3-(3-diethylamino-1-propyl)-5-(3-diethylamino-1-propoxy)benzimidazole (160 mg). LC: Tr 1.90 min; MS: m/z 687.0 (M+H).

EXAMPLE 11

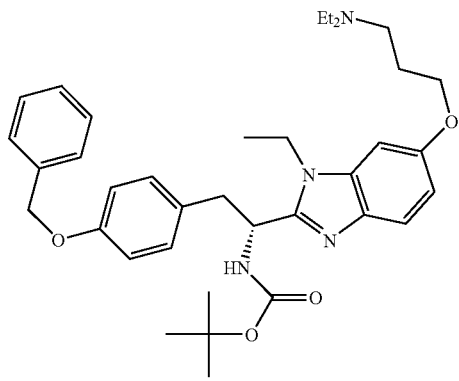

A solution of 2-fluoro-4-(3-diethylamino-1-propoxy)nitrobenzene (2 mmol; preparation described in Example 5) in THF (5 mL) is treated with ethylamine (4 mmol) at rt. After completion of the reaction, the reaction mixture is concentrated in vacuo. The residue is redissolved in EtOAc (10 mL), washed with saturated sodium bicarbonate solution, water, and brine. The organic phase is then dried over sodium sulfate and the solvent is removed in vacuo to afford the product, 2-(ethylamino)-4-(3-diethylamino-1-propoxy)nitrobenzene (520 mg) which was used for further transformation without further purification.

The nitroamine obtained as above (1.0 mmol) is dissolved in EtOH (5 mL) and added with 10% Pd/C (100 mg). The reaction mixture is hydrogenated as in the general procedure III (Step C) to obtain the product, 2-(ethylamino)-4-(3-diethylamino-1-propoxy)aniline (240 mg).

A mixture of the diamine formed as above (0.5 mmol) and the aldehyde (0.5 mmol) obtained from the reduction of BOC-(O-benzyl)-Tyr-OH (described earlier) are used according to the general procedure IV to afford the product, 2-[(1R)-2-(4-Benzyloxyphenyl)-1-(tert-butoxycarbonylamino)-1-ethyl]-3-ethyl-5-(3-diethylamino-1-propoxy)benzimidazole (140 mg). LC: Tr 2.01 min; MS: m/z 602.0 (M+H).

EXAMPLE 12

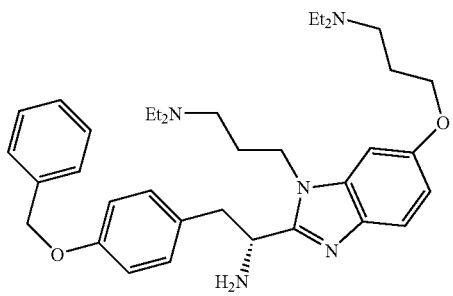

50 mg of the Example 10 is stirred in 4 M HCl in dioxane (1 mL) overnight. Solvent is then removed in vacuo and the residue obtained is triturated with ether and stirred. The ether is decanted off and the ether wash is repeated twice more. The product is then dried under vacuum to afford the 2-[(1R)-2-(4-Benzyloxyphenyl)-1-amino-1-ethyl]-3-(3-diethylamino-1-propyl)-5-(3-diethylamino-1-propoxy)benzimidazole as hydrochloride salt (35 mg). LC: Tr 0.85 min; MS: m/z 587.0 (M+H).

EXAMPLE 13

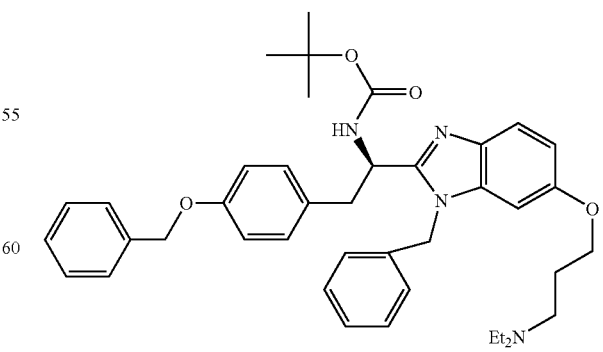

A solution of 2-fluoro-4-(3-diethylamino-1-propoxy)nitrobenzene (2 mmol; preparation described in Example 5) in THF (5 mL) is treated with benzylamine (2.4 mmol) at rt. After completion of the reaction, the reaction mixture is concentrated in vacuo. The residue is redissolved in EtOAc (10 mL), washed with saturated sodium bicarbonate solution, water, and brine. The organic phase is then dried over sodium sulfate and the solvent is removed in vacuo to afford the product, 2-(benzylamino-4-(3-diethylamino-1-propoxy) nitrobenzene (620 mg) which was used for further transformation without further purification.

The nitroamine (1 mmol) obtained as above is dissolved in ethanol (10 mL) and treated with tin (II) chloride dihydrate (5 mmol). The contents are then refluxed overnight according to the general procedure II (Step B). The crude aniline (280 mg) is used for further transformation without any purification.

A mixture of the diamine formed as above (0.5 mmol) and the aldehyde (0.5 mmol) obtained from the reduction of BOC-(O-benzyl)-Tyr-OH (described earlier) are used according to the general procedure IV to afford the product, 2-[(1R)-2-(4-Benzyloxyphenyl)-1-(tert-butoxycarbonylamino)-1-ethyl]-3-benzyl-5-(3-diethylamino-1-propoxy) benzimidazole (160 mg). LC: Tr 2.04 min; MS: m/z 664.0 (M+H).

EXAMPLE 14

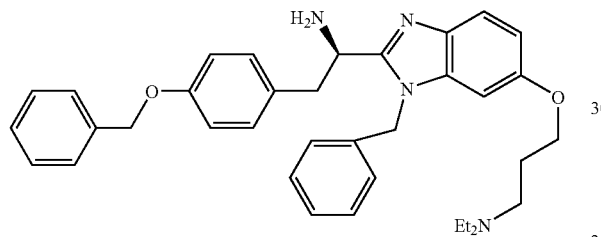

45 mg of the Example 13 is stirred in 4 M HCl in dioxane (1 mL) overnight. Solvent is then removed in vacuo and the residue obtained is triturated with ether and stirred. The ether is decanted off and the ether wash is repeated twice more. The product is then dried under vacuum to afford the 2-[(1R)-2-(4-Benzyloxyphenyl)-1-amino-1-ethyl]-3-benzyl-5-(3-diethylamino-1-propoxy)benzimidazole as hydrochloride salt (30 mg). LC: Tr 1.97 min; MS: m/z 564.0 (M+H).

EXAMPLE 15

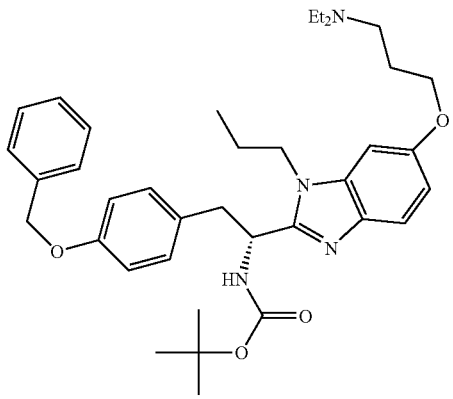

A solution of 2-fluoro-4-(3-diethylamino-1-propoxy)nitrobenzene (2 mmol; preparation described in Example 5) in THF (5 mL) is treated with propylamine (3 mmol) at rt. After completion of the reaction, the reaction mixture is concentrated in vacuo. The residue is redissolved in EtOAc (10 mL), washed with saturated sodium bicarbonate solution, water, and brine. The organic phase is then dried over sodium sulfate and the solvent is removed in vacuo to afford the product, 2-(propylamino)-4-(3-diethylamino-1-propoxy) nitrobenzene (540 mg) which was used for further transformation without further purification.

The nitroamine obtained as above (1.0 mmol) is dissolved in EtOH (5 mL) and added with 10% Pd/C (100 mg). The reaction mixture is hydrogenated as in the general procedure III (Step C) to obtain the product, 2-(propylamino)-4-(3-diethylamino-1-propoxy)aniline (270 mg).

A mixture of the diamine formed as above (0.5 mmol) and the aldehyde (0.5 mmol) obtained from the reduction of BOC-(O-benzyl)-Tyr-OH (described earlier) are used according to the general procedure IV to afford the product, 2-[(1R)-2-(4-Benzyloxyphenyl-1-(tert-butoxycarbonylamino)-1-ethyl]-3-propyl-5-(3-diethylamino-1-propoxy) benzimidazole (150 mg). LC: Tr 2.1 min; MS: m/z 616.0 (M+H).

EXAMPLE 16

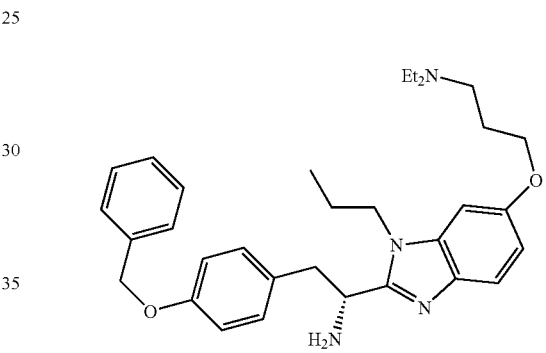

45 mg of the Example 15 is stirred in 4 M HCl in dioxane (1 mL) overnight. Solvent is then removed in vacuo and the residue obtained is triturated with ether and stirred. The ether is decanted off and the ether wash is repeated twice more. The product is then dried under vacuum to afford the 2-[(1R)-2-(4-Benzyloxyphenyl)-1-amino-1-ethyl]-3-propyl-5-(3-diethylamino-1-propoxy)benzimidazole as hydrochloride salt (35 mg). LC: Tr 1.82 min; MS: m/z 516.0 (M+H).

Biological Assay

The following assay method is utilized to identify compounds of Formula (I) which are effective in binding with RAGE, and hence useful as modulators, preferably antagonists of RAGE. This method is also described and claimed in co-pending U.S. Ser. No. 09/799,152 filed on this date.

General Assay Procedure

S100b, β-amyloid and CML (500 ng/100 μL/well) in 100 mM sodium bicarbonate/sodium carbonate buffer (pH 9.8) is loaded onto the wells of a NUNC Maxisorp flat bottom 96-well microtitre plate. The plate is incubated at 4° C. overnight. The wells are aspirated and treated with 50 mM imidazole buffer saline (pH 7.2) (with 1 mM $CaCl_2/MgCl_2$) containing 1% bovine serum albumin (BSA) (300 μL/well) for two h at 37° C. The wells are aspirated and washed 3 times (400 μL/well) with 155 mM NaCl pH 7.2 buffer saline and soaked 10 seconds between each wash.

Test compounds are dissolved in nanopure water (concentration: 10-100 μM). DMSO may be used as co-solvent. 25 μL of test compound solution in 2% DMSO is added, along with 75 μL sRAGE ($4.0 \times 10^{-4}$ mg/mL FAC) to each well and samples are incubated for 1 h at 37° C. The wells are washed 3 times with 155 mM NaCl pH 7.2 buffer saline and are soaked 10 seconds between each wash.

Non-Radioactive Binding is Performed by Adding:

10 μL Biotinylated goat F(ab')2 Anti-mouse IgG. ($8.0 \times 10^{-4}$ mg/mL, FAC)

10 μL Alkaline phosphatase Sterptavidin ($3 \times 10^{-3}$ mg/mL FAC)

10 μL Polyclonal antibody for sRAGE (FAC $6.0 \times 10^{-3}$ mg/mL)

to 5 mL 50 mM imidazole buffer saline (pH 7.2) containing 0.2% bovine serum albumin and 1 mM $CaCl_2$. The mixture is incubated for 30 minutes at 37° C. 100 μL complex is added to each well and incubation is allowed to proceed at rt for 1 h. Wells are washed 3 times with wash buffer and soaked 10 s between each wash. 100 μL 1 mg/mL (pNPP) in 1 M diethanolamine (pH adjusted to 9.8 with HCl) is added. Color is allowed to develop in the dark for 1 to 2 h at rt. The reaction is quenched with 10 μL of stop solution (0.5 N NaOH in 50% ethanol) and the absorbance is measured spectrophotometrically with a microplate reader at 405 nm.

The following compounds of Formula 1 were tested according to the assay method described above.

$IC_{50}$ (μM) of ELISA assay represents the concentration of compound at which 50% signal has been inhibited.

| | ELISA Assay $IC_{50}$ (μM) | | |
|---|---|---|---|
| Example No. | S-100b | Amyloid-β | Carboxymethyl Lysine (CML) |
| 1 | +++ | +++ | ++++ |
| 2 | +++ | +++ | +++ |
| 3 | +++ | +++ | +++ |
| 4 | +++ | +++ | +++ |
| 5 | + | NA | ++ |
| 6 | ++ | ++ | +++ |
| 7 | +++ | +++ | +++ |
| 8 | ++ | ++ | +++ |
| 9 | ++++ | ++++ | ++++ |
| 10 | +++ | ++ | +++ |
| 11 | +++ | +++ | +++ |
| 12 | +++ | +++ | +++ |
| 13 | ++ | ++ | ++ |
| 14 | ++ | + | ++ |
| 15 | ++ | ++ | ++ |
| 16 | ++ | + | + |

NA = ELISA assay data not available
Key
+++++ <0.5 μM
++++ Between 0.5 μM and 1 μM
+++ Between 1 μM and 5 μM
++ Between 5 μM and 10 μM
+ Between 10 μM and 20 μM The invention further provides pharmaceutical compositions comprising the RAGE modulating compounds of the invention. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166, 452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or welting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or welting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions or suspensions, etc., containing the compounds of the invention are contemplated. For the purpose of this application, topical applications shall include mouth washes and gargles. The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines. Also provided by the present invention are prodrugs of the invention.

Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Methanesulfonate, Methylbromide, Methyinitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1-19.

Other salts which are not pharmaceutically acceptable may be useful in the preparation of compounds of the invention and these form a further aspect of the invention.

In addition, some of the compounds of the present invention may form solvates with water or common organic solvents. Such solvates are also encompassed within the scope of the invention.

Thus, in a further embodiment, there is provided a pharmaceutical composition comprising a compound of the present invention, or a pharmaceutically acceptable salt, solvate, or prodrug thereof, and one or more pharmaceutically acceptable carriers, excipients, or diluents.

The compounds of the present invention selectively act as modulators of RAGE binding to a single endogenous ligand, i.e., selective modulators of β-amyloid-RAGE interaction, and therefore are especially advantageous in treatment of Alzheimer's disease and related dementias.

Further, the compounds of the present invention act as modulators of RAGE interaction with two or more endogenous ligands in preference to others. Such compounds are advantageous in treatment of related or unrelated pathologies mediated by RAGE, i.e., Alzheimer's disease and cancer.

Further, the compounds of the present invention act as modulators of RAGE binding to each and every one of its ligands, thereby preventing the generation of oxidative stress and activation of NF-κB regulated genes, such as the cytokines IL-1, and TNF-α. Thus, antagonizing the binding of physiological ligands to RAGE prevent targeted pathophysiological consequences and useful for management or treatment of diseases, i.e., AGE-RAGE interaction leading to diabetic complications, S100/EN-RAGE/calgranulin-RAGE interaction leading to inflammatory diseases, β-amyloid-RAGE interaction leading to Alzheimer's Disease, and amphoterin-RAGE interaction leading to cancer.

I. RAGE and the Complications of Diabetes

As noted above, the compounds of the present invention are useful in the treatment of the complications of diabetes. It has been shown that nonenzymatic glycoxidation of macromolecules ultimately resulting in the formation of advanced glycation endproducts (AGEs) is enhanced at sites of inflammation, in renal failure, in the presence of hyperglycemia and other conditions associated with systemic or local oxidant stress (Dyer, D., et al., *J. Clin. Invest.,* 91:2463-2469 (1993); Reddy, S., et al., *Biochem.,* 34:10872-10878 (1995); Dyer, D., et al., *J. Biol. Chem.,* 266:11654-11660 (1991); Degenhardt, T., et al., *Cell Mol. Biol.,* 44:1139-1145 (1998)). Accumulation of AGEs in the vasculature can occur focally, as in the joint amyloid composed of AGE-$\beta_2$-microglobulin found in patients with dialysis-related amyloidosis (Miyata, T., et al., *J. Clin. Invest,* 92:1243-1252 (1993); Miyata, T., et al, *J. Clin. Invest,* 98:1088-1094 (1996)), or generally, as exemplified by the vasculature and tissues of patients with diabetes (Schmidt, A.-M., et al., *Nature Med.,* 1:1002-1004 (1995)). The progressive accumulation of AGEs overtime in patients with diabetes suggests that endogenous clearance mechanisms are not able to function effectively at sites of AGE deposition. Such accumulated AGEs have the capacity to alter cellular properties by a number of mechanisms. Although RAGE is expressed at low levels in normal tissues and vasculature, in an environment where the receptor's ligands accumulate, it has been shown that RAGE becomes upregulated (Li, J. et al., *J. Biol. Chem.,* 272:16498-16506 (1997); Li, J., et al., *J. Biol. Chem.,* 273:30870-30878 (1998); Tanaka, N., et al., *J. Biol. Chem,.* 275:25781-25790(2000)). RAGE expression is increased in endothelium, smooth muscle cells and infiltrating mononuclear phagocytes in diabetic vasculature. Also, studies in cell culture have demonstrated that AGE-RAGE interaction caused changes in cellular properties important in vascular homeostasis.

II. RAGE and Cellular Dysfunction in the Amyloidoses

Also as noted above, the compounds of the present invention are useful in treating amyloidoses and Alzheimer's disease. RAGE appears to be a cell surface receptor which binds β-sheet fibrillar material regardless of the composition of the subunits (amyloid-β peptide, Aβ, amylin, serum amyloid A, prion-derived peptide) (Yan, S.-D., et al., *Nature,* 382:685-691 (1996); Yan, S-D., et al., *Nat. Med.,* 6:643-651 (2000)). Deposition of amyloid has been shown to result in enhanced expression of RAGE. For example, in the brains of patients with Alzheimer's disease (AD), RAGE expression increases in neurons and glia (Yan, S. -D., et al., *Nature* 382:685-691 (1996)). The consequences of Aβ interaction with RAGE appear to be quite different on neurons versus microglia. Whereas microglia become activated as a consequence of Aβ-RAGE interaction, as reflected by increased motility and expression of cytokines, early RAGE-mediated neuronal activation is superceded by cytotoxicity at later times. Further evidence of a role for RAGE in cellular interactions of Aβ concerns inhibition of Aβ-induced cerebral vasoconstriction and transfer of the peptide across the blood-brain barrier to brain parenchyma when the receptor was blocked (Kumar, S., et al., *Neurosci. Program, p* 141-#275.19 (2000)). Inhibition of RAGE-amyloid interaction has been shown to decrease expression of cellular RAGE and cell stress markers (as well as NF-κB activation), and diminish amyloid deposition (Yan, S-D., et al., *Nat. Med.,* 6:643-651 (2000)) suggesting a role for RAGE-amyloid interaction in both perturbation of cellular properties in an environment enriched for amyloid (even at early stages) as well as in amyloid accumulation.

III. RAGE and Propagation of the Immune/Inflammatory Response

As noted above, the compounds of the present invention are useful in treating inflammation. For example, S100/calgranulins have been shown to comprise a family of closely related calcium-binding polypeptides characterized by two EF-hand regions linked by a connecting peptide (Schafer, B. et al., *TIBS,* 21:134-140 (1996); Zimmer, D., et al., *Brain Res. Bull.,* 37:417-429 (1995); Rammes, A., et al., *J. Biol. Chem.,* 272:9496-9502 (1997); Lugering, N., et al., *Eur. J. Clin. Invest.,* 25:659-664 (1995)). Although they lack signal peptides, it has long been known that S100/calgranulins gain access to the extracellular space, especially at sites of chronic immune/inflammatory responses, as in cystic fibrosis and rheumatoid arthritis. RAGE is a receptor for many members of the S100/calgranulin family, mediating their proinflammatory effects on cells such as lymphocytes and mononuclear phagocytes. Also, studies on delayed-type hypersensitivity response, colitis in IL-10 null mice, collagen-induced arthritis, and experimental autoimmune encephalitis models suggest that RAGE-ligand interaction (presumably with S100/calgranulins) has a proximal role in the inflammatory cascade.

IV. RAGE and Amphoterin

As noted above, the compounds of the present invention are useful in treating tumor and tumor metastasis. For example, amphoterin is a high mobility group I nonhistone chromosomal DNA binding protein (Rauvala, H., et a., *J. Biol. Chem.,* 262:16625-16635 (1987); Parkikinen, J., et al., *J. Biol. Chem.* 268:19726-19738 (1993)) which has been shown to interact with RAGE. It has been shown that amphoterin promotes neurite outgrowth, as well as serving as a surface for assembly of protease complexes in the fibrinolytic system (also known to contribute to cell mobility). In addition, a local tumor growth inhibitory effect of blocking RAGE has been observed in a primary tumor model (C6 glioma), the Lewis lung metastasis model (Taguchi, A., et al., *Nature* 405:354-360 (2000)), and spontaneously arising papillomas in mice expressing the v-Ha-ras transgene (Leder, A., et al, *Proc. Natl. Acad. Sci.,* 87:9178-9182 (1990)).

Amphoterin is a high mobility group I nonhistone chromosomal DNA binding protein (Rauvala, H. and R. Pihlaskari. 1987. Isolation and some characteristics of an adhesive factor of brain that enhances neurite outgrowth in central neurons. *J. Biol. Chem.* 262:16625-16635. (Parkikinen, J., E. Raulo, J. Merenmies, R. Nolo, E. Kajander, M. Baumann, and H. Rauvala. 1993. Amphoterin, the 30 kDa protein in a family of HIMG1-type polypeptides. *J. Biol. Chem.* 268:19 726-19738).

V. RAGE and Erectile Dysfunction

Relaxation of the smooth muscle cells in the cavernosal arterioles and sinuses results in increased blood flow into the penis, raising corpus cavernosum pressure to culminate in penile erection. Nitric oxide is considered the principle stimulator of cavernosal smooth muscle relaxation (See Wingard C J, Clinton W, Branam H, Stopper V S, Lewis R W, Mills T M, Chitaley K. Antagonism of Rho-kinase stimulates rat penile erection via a nitric oxide-independent pathway. Nature Medicine January 2001; 7(1):119-122). RAGE activation produces oxidants (See Yan, S.-D., Schmidt A-M., Anderson, G., Zhang, J., Brett, J., Zou, Y-S., Pinsky, D., and Stern, D. Enhanced cellular oxidant stress by the interaction of advanced glycation endproducts with their receptors/binding proteins. J. Biol. Chem. 269:9889-9887, 1994.) via an NADH oxidase-like enzyme, therefore suppressing the circulation of nitric oxide. Potentially by inhibiting the activation of RAGE signaling pathways by decreasing the intracellular production of AGEs, generation of oxidants will be attenuated. RAGE blockers may promote and facilitate penile erection by blocking the access of ligands to RAGE.

The calcium-sensitizing Rho-kinase pathway may play a synergistic role in cavernosal vasoconstriction to maintain penile flaccidity. The antagonism of Rho-kinase results in increased corpus cavernosum pressure, initiating the erectile response independently of nitric oxide (Wingard et al.). One of the signaling mechanisms activated by RAGE involves the Rho-kinase family such as cdc42 and rac (See Huttunen H J, Fages C, Rauvala H. Receptor for advanced glycation end products (RAGE)-mediated neurite outgrowth and activation of NF-kappaB require the cytoplasmic domain of the receptor but different downstream signaling pathways. J Biol Chem 1999 Jul. 9; 274(28):19919-24). Thus, inhibiting activation of Rho-kinases via suppression of RAGE signaling pathways will enhance and stimulate penile erection independently of nitric oxide.

Thus, in a further aspect, the present invention provides a method for the inhibition of the interaction of RAGE with physiological ligands. In a preferred embodiment of this aspect, the present invention provides a method for treating a disease state selected from the group consisting of acute and chronic inflammation, vascular permeability, nephropathy, atherosclerosis, retinopathy, Alzheimer's disease, erectile dysfunction, and tumor invasion and/or metastasis, which comprises administering to a subject in need thereof a compound of the present invention, preferably a pharmacologically effective amount, more preferably a therapeutically effective amount. In a preferred embodiment, at least one compound of Formula (I) is utilized, either alone or in combination with one or more known therapeutic agents. In a further preferred embodiment, the present invention provides method of prevention and/or treatment of RAGE mediated human diseases, treatment comprising alleviation of one or more symptoms resulting from that disorder, to an outright cure for that particular disorder or prevention of the onset of the disorder, the method comprising administration to a human in need thereof a therapeutically effective amount of a compound of the present invention, preferably a compound of Formula (I).

In this method, factors which will influence what constitutes an effective amount will depend upon the size and weight of the subject, the biodegradability of the therapeutic agent, the activity of the therapeutic agent, as well as its bioavailability. As used herein, the phrase "a subject in need thereof" includes mammalian subjects, preferably humans, who either suffer from one or more of the aforesaid diseases or disease states or are at risk for such. Accordingly, in the context of the therapeutic method of the invention, this method also is comprised of a method for treating a mammalian subject prophylactically, or prior to the onset of diagnosis such disease(s) or disease state(s).

In a further aspect of the present invention, the RAGE modulators of the invention are utilized in adjuvant therapeutic or combination therapeutic treatments with other known therapeutic agents.

The term "treatment" as used herein, refers to the full spectrum of treatments for a given disorder from which the patient is suffering, including alleviation of one, most of all symptoms resulting from that disorder, to an outright cure for the particular disorder or prevention of the onset of the disorder.

The following is a non-exhaustive listing of adjuvants and additional therapeutic agents which may be utilized in combination with the RAGE modulators of the present invention:

Pharmacologic Classifications of Anticancer Agents:
1. Alkylating agents: Cyclophosphamide, nitrosoureas, carboplatin, cisplatin, procarbazine
2. Antibiotics: Bleomycin, Daunorubicin, Doxorubicin
3. Antimetabolites: Methotrexate, Cytarabine, Fluorouracil
4. Plant alkaloids: Vinblastine, Vincristine, Etoposide, Paclitaxel,
5. Hormones: Tamoxifen, Octreotide acetate, Finasteride, Flutamide
6. Biologic response modifiers: Interferons, Interleukins, Pharmacologic Classifications of Treatment for Rheumatoid Arthritis (Inflammation)
1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids Pharmacologic Classifications of Treatment for Diabetes Mellitus
1. Sulfonylureas: Tolbutamide, Tolazamide, Glyburide, Glipizide
2. Biguanides: Metformin
3. Miscellaneous oral agents: Acarbose, Troglitazone
4. Insulin Pharmacologic Classifications of Treatment for Alzheimer's Disease
1. Cholinesterase Inhibitor: Tacrine, Donepezil
2. Antipsychotics: Haloperidol, Thioridazine
3. Antidepressants: Desipramine, Fluoxetine, Trazodone, Paroxetine
4. Anticonvulsants: Carbamazepine, Valproic acid In a further preferred embodiment, the present invention provides a method of treating RAGE mediated diseases, the method comprising administering to a subject in need thereof, a therapeutically effective amount of a compound of Formula (I) in combination with therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants. In a further preferred embodiment, the present invention provides the pharmaceutical composition of the invention as described above, further comprising one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

Generally speaking, the compound of the present invention, preferably Formula (I), is administered at a dosage level of from about 0.01 to 500 mg/kg of the body weight of the subject being treated, with a preferred dosage range between 0.01 and 200 mg/kg, most preferably 0.1 to 100 mg/kg of body weight per day. The amount of active ingredient that may be combined with the carrier materials to produce a single dosage will vary depending upon the host treated and the particular mode of administration. For example, a formulation intended for oral administration to humans may contain 1 mg to 2 grams of a compound of Formula (I) with an appropriate and convenient amount of carrier material which may vary from about 5 to 95 percent of the total composition. Dosage unit forms will generally contain between from about 5 mg to about 500 mg of active ingredient. This dosage has to be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein may be applicable as a consequence of variations in the responsiveness of the mammal being treated for RAGE-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:

1. A pharmaceutical composition comprising the compound of Formula (II)

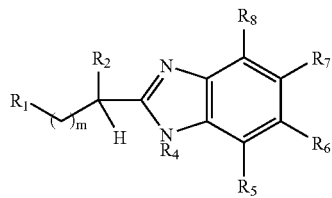

wherein
m is an integer of from 0 to 3;
$R_1$ is an aryl group;
$R_2$ is a group of the formula —N($R_9R_{10}$), —NHC(O)$R_9$, or —NHC(O)O$R_9$;
wherein $R_9$ and $R_{10}$ are independently selected from the group consisting of
1) —H;
2) -Aryl;
3) —$C_{1-6}$ alkyl; and
4) —$C_{1-6}$ alkylaryl;
$R_4$ is
a) H;
b) -aryl;
c) —$C_{1-6}$ alkyl;
d) —$C_{1-6}$ alkylaryl; or
e) —$C_{1-6}$ alkoxyaryl;
$R_5$, $R_6$, $R_7$, and $R_8$ are independently selected from the group consisting of a) —H;
b) —$C_{1-6}$ alkyl;
c) -aryl;
d) —$C_{1-6}$ alkylaryl;
e) —C(O)—O—$C_{1-6}$ alkyl;
f) —C(O)—O—$C_{1-6}$ alkylaryl;
g) —C(O)—NH—$C_{1-6}$ alkyl;
h) —C(O)—NH—$C_{1-6}$ alkylaryl;
i) —$SO_2$—$C_{1-6}$ alkyl;
j) —$SO_2$—$C_{1-6}$ alkylaryl;
k) —$SO_2$-aryl;
l) —$SO_2$—NH—$C_{1-6}$ alkyl;
m) —$SO_2$—NH—$C_{1-6}$ alkylaryl;
n) —C(O)—$C_{1-6}$ alkyl;
o) —C(O)—$C_{1-6}$ alkylary;
p) —Y—$C_{1-6}$ alkyl;
q) —Y-aryl;
r) —Y—$C_{-1-6}$ alkylaryl;
s) —Y—$C_{1-6}$ alkylene-$NR_{13}R_{14}$;
t) —Y—$C_{1-6}$ alklene-W—$R_{15}$;
wherein Y and W are independently selected from the group consisting of —$CH_2$—, —O—, —N(H), —S—, —$SO_2$—, —CON(H)—, —NHC(O)—, —NHCON(H)—, —$NHSO_2$—, —$SO_2N(H)$—, —C(O)—O—, —$NHSO_2NH$—, —O—CO—,

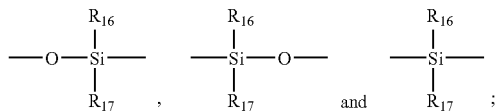

wherein $R_{16}$ and $R_{17}$ are independently selected from the group consisting of aryl, $C_1$-$C_6$alkyl, $C_1$-$C_6$ alkylaryl, $C_1$-$C_6$ alkoxy, and $C_1$-$C_6$alkoxyaryl,
$R_{15}$ is aryl, $C_1$-$C_6$ alkyl, or $C_1$-$C_6$ alkylaryl, and
u) halogen, hydroxyl, cyano, carbamoyl, and carboxyl;
wherein at least one of $R_5$, $R_6$, $R_7$, and $R_8$ is —Y—$C_{1-6}$ alkylene-N—$R_{13}R_{14}$,
$R_{13}$, and $R_{14}$ are independently selected from the group consisting of hydrogen, aryl, $C_1$-$C_6$ alkyl, $C_1$-$C_6$ alkylaryl, $C_1$-$C_6$ alkoxy, and $C_1$-$C_6$ alkoxyaryl; or
$R_{13}$ and $R_{14}$ are taken together to form a ring having the formula —$(CH_2)_o$—X—$(CH_2)_p$— bonded to the nitrogen atom to which $R_{13}$ and $R_{14}$ are attached, wherein o and p are, independently, 1, 2, 3, or 4; X is a direct bond, —$CH_2$—, —O—, —S—, —$SO_2$—, —C(O)—, —CON(H)—, —NHC(O)—, —NHCON(H)—, —$NHSO_2$—, —$SO_2N(H)$—, —C(O)—O—, —O—C(O)—, —$NHSO_2NH$—,

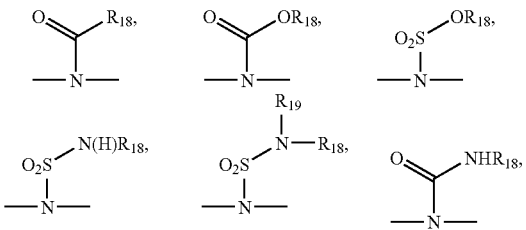

-continued

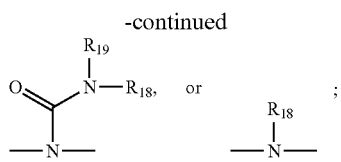
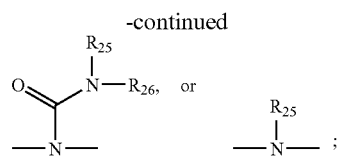

wherein $R_{18}$ and $R_{19}$ are alkyl or aryl;

and wherein the aryl and/or alkyl group(s) in $R_4$, $R_5$, $R_6$, $R_7$, $R_8$, $R_9$, $R_{10}$, $R_{13}$, $R_{14}$, $R_{15}$, $R_{16}$, $R_{17}$, $R_{18}$, and $R_{19}$ may be optionally substituted 1-4 times with a substituent group, wherein said substituent group(s) or the term substituted refers to groups selected from the group consisting of:

a) —H;
b) —Z—$C_{1-6}$ alkyl;
—Z-aryl;
—Z—$C_{1-6}$ alkylaryl;
—Z—$C_{1-6}$-alkyl-$NR_{20}R_{21}$;
—Z—$C_{1-6}$-alkyl-W—$R_{22}$;
wherein Z and W are independently selected from the group consisting of —$CH_2$—, —O—, —N(H)—, —S—, —$SO_2$—, —CON(H)—, —NHC(O)—, —NHCON(H)—, —$NHSO_2$—, —$SO_2$N(H)—, —C(O)—O—, —$NHSO_2$NH—, —O—CO—,

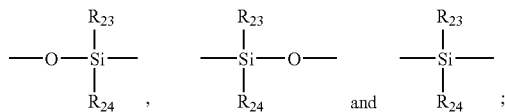

wherein,
$R_{22}$, $R_{23}$, and $R_{24}$ are independently selected from the group consisting of aryl, $C_1$-$C_6$ alkyl, $C_1$-$C_6$ alkylaryl, $C_1$-$C_6$ alkoxy, and $C_1$-$C_6$ alkoxyaryl, c) halogen, hydroxyl, cyano, and carbamoyl, and wherein $R_{20}$ and $R_{21}$ are independently selected from the group consisting of hydrogen, aryl, $C_1$-$C_6$ alkyl, $C_1$-$C_6$ alkylaryl, $C_1$-$C_6$ alkoxy, and $C_1$-$C_6$ alkoxyaryl; or $R_{20}$ and $R_{21}$ are taken together to form a ring having the formula —$(CH_2)_q$—X—$(CH_2)_r$— bonded to the nitrogen atom to which $R_{20}$ and $R_{21}$ are attached wherein q and r are, independently, 1, 2, 3, or 4; X is a direct bond, —$CH_2$—, —O—, —S—, —$SO_2$—, —C(O)—, —CON(H)—, —NHC(O)—, —NHCON(H)—, —$NHSO_2$—, —$SO_2$N(H)—, —C(O)—O—, —O—C(O)—, —$NHSO_2$NH—,

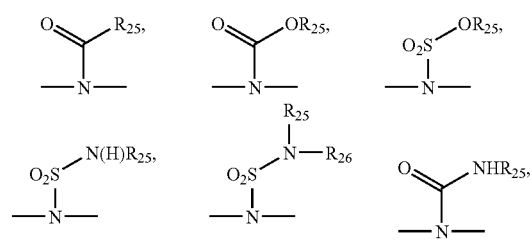

$R_{25}$ and $R_{26}$ are independently selected from the group consisting of hydrogen, aryl, $C_1$-$C_6$ alkyl, and $C_1$-$C_6$ alkylaryl; or a pharmaceutically acceptable salt, solvate or prodrug thereof, and one or more pharmaceutically acceptable carriers, excipients, or diluents.

2. The pharmaceutical composition of to claim 1, in the form of an oral dosage or parenteral dosage unit.

3. The pharmaceutical composition of claim 1, wherein said compound is administered as a dose in a range from about 0.01 to 500 mg/kg of body weight per day.

4. The pharmaceutical composition of claim 1, wherein said compound is administered as a dose in a range from about 0.1 to 200 mg/kg of body weight per day.

5. The pharmaceutical composition of claim 1, wherein said compound is administered as a dose in a range from about 0.1 to 100 mg/kg of body weight per day.

6. The pharmaceutical composition of claim 1, further comprising one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

7. The pharmaceutical composition of claim 1, wherein $R_4$ is
a) aryl;
b) —$C_{1-6}$ alkyl;
c) —$C_{1-6}$ alkylaryl; or
d) —$C_{1-6}$ alkylaryl.

8. The pharmaceutical composition of claim 1, wherein the compound of Formula (II) is 2-[(1R)-2-(4-Benzyloxyphenyl)-1-tert-butoxycarbonylamino-1-ethyl]-3-butyl-5-(3-diethylamino-1-propoxy)benzimidazole, or a pharmaceutically acceptable salt, solvate or prodrug thereof.

9. The pharmaceutical composition of claim 1, wherein the compound of Formula (II) is 2-[(1R)-2-(4-Benzyloxyphenyl)-1-amino-1-ethyl]-3-butyl-5-(3-diethylamino-1-propoxy)benzimidazole, or a pharmaceutically acceptable salt, solvate or prodrug thereof.

10. The pharmaceutical composition of claim 1, wherein the compound of Formula (II) is 2-[(1R)-2-(4-Benzyloxyphenyl)-1-tert-butoxycarbonylamino-1-ethyl]-3-butyl-6-(3-diethylamino-1-propoxy)benzimidazole, or a pharmaceutically acceptable salt, solvate or prodrug thereof.

11. The pharmaceutical composition of claim 1, wherein the compound of Formula (II) is 2-[(1R)-2-(4-Benzyloxyphenyl)-1-amino-1ethyl]-3-butyl-6-(3-diethylamino-1-propoxy)benzimidazole, or a pharmaceutically acceptable salt, solvate or prodrug thereof.

12. The pharmaceutical composition of claim 1, wherein the compound of Formula (II) is 2-[(1R)-2-(4-Benzyloxyphenyl)-tert-butoxycarbonylamino-1-ethyl]-6-(3-diethylamino-1-propoxy)benzimidazole, or a pharmaceutically acceptable salt, solvate or prodrug thereof.

13. The pharmaceutical composition of claim 1, wherein the compound of Formula (II) is 2-[(1R)-2-(4-Benzyloxyphenyl)-1-amino-1-ethyl]-6-(3-diethylamino-1-propoxy) benzimidazole, or a pharmaceutically acceptable salt, solvate or prodrug thereof.

14. The pharmaceutical composition of claim 1, wherein the compound of Formula (II) is 2-[2-(3-Benzyloxyphenyl)-1-(tert-butoxycarbonylamino)-1-ethyl]-3butyl-5(3-diethlamino-1-propoxy)benzimidazole, or a pharmaceutically acceptable salt, solvate or prodrug thereof.

15. The pharmaceutical composition of claim 1, wherein the compound of Formula (II) is 2-[(1R)-2-(4-Ethoxyphenyl)-1-(tert-butoxycarbonylamino)-1-ethyl]-3-butyl-5-(3-diethylamino-1-propoxy)benzimidazole, or a pharmaceutically acceptable salt, solvate or prodrug thereof.

16. The pharmaceutical composition of claim 1, wherein the compound of Formula (II) is 2-[(1R)-2-(4-(4-Chloro)phenethoxy)phenyl)-1-(tert-butoxycarbonylamino)-1-ethyl]-3-butyl-5-(3-diethylamino-1-propoxy)benzimidazole, or a pharmaceutically acceptable salt, solvate or prodrug thereof.

17. The pharmaceutical composition of claim 1, wherein the compound of Formula (II) is 2-[(1R)-2-(4-Benzyloxyphenyl)-1-(tert-butoxycarbonylamino)-1-ethyl]-3-(3-diethylamino-1-propyl)-5-(3-diethylamino-1-propoxy)benzimidazole, or a pharmaceutically acceptable salt, solvate or prodrug thereof.

18. The pharmaceutical composition of claim 1, wherein the compound of Formula (II) is 2-[(1R)-2-(4-Benzyloxyphenyl)-1-(tert-butoxycarbonylamino)-1-ethyl]-3-ethyl-5-(3-diethylamino-1-propoxy)benzimidazole, or a pharmaceutically acceptable salt, solvate or prodrug thereof.

19. The pharmaceutical composition of claim 1, wherein the compound of Formula (II) is 2-[(1R)-2-(4-Benzyloxyphenyl)-1-amino-1-ethyl]-3-(3-diethylamino-1-propyl)-5-(3-diethylamino-1-propoxy)benzimidazole, or a pharmaceutically acceptable salt, solvate or prodrug thereof.

20. The pharmaceutical composition of claim 1, wherein the compound of Formula (II) is 2-[(1R)-2-(4-Benzyloxyphenyl)-1-(tert-butoxycarbonylamino)-1ethyl]-3-benzyl-5-(3-diethylamino-1-propoxy)benzimidazole, or a pharmaceutically acceptable salt, solvate or prodrug thereof.

21. The pharmaceutical composition of claim 1, wherein the compound of Formula (II) is 2-[(1R)-2-(4-Benzyloxphenyl)-1amino-1-ethyl]-3-benzyl-5-(3-diethylamino-1-propoxy)benzimidazole, or a pharmaceutically acceptable salt, solvate or prodrug thereof.

22. The pharmaceutical composition of claim 1, wherein the compound of Formula (II) is 2-[(1R)-2-4-Benzyloxyphenyl)-1-(tert-butoxycarbonylamino)-1ehtyl]-3-propyl-5-(3-diethylamino-1-propoxy)benzimidazole, or a pharmaceutically acceptable salt, solvate or prodrug thereof.

23. The pharmaceutical composition of claim 1, wherein the compound of Formula (II) is 2-[(1R)-2-(4-Benzyloxyphenyl)-1-amino-1-ethyl]-3-propyl-5-(3-diethylamino-1-propoxy)benzimidazole, or a pharmaceutically acceptable salt, solvate or prodrug thereof.

* * * * *